(12) United States Patent
Fujimori et al.

(10) Patent No.: US 6,628,380 B1
(45) Date of Patent: Sep. 30, 2003

(54) APPEARANCE INSPECTING JIG FOR SMALL PARTS AND INSPECTING METHOD EMPLOYING THE SAME JIG

(75) Inventors: Masashi Fujimori, Fujisawa (JP); Kenji Itoh, Fujisawa (JP); Toru Koike, Chigasaki (JP); Yuhsuke Matsumoto, Fujisawa (JP); Seiji Nakagawa, Kanagawa-ken (JP); Tatsumi Tsuchiya, Kanagawa-ken (JP); Tatsushi Yoshida, Kanagawa-ken (JP)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/897,183

(22) Filed: Jul. 2, 2001

(30) Foreign Application Priority Data

Jul. 3, 2000 (JP) .................................. 2000-200861

(51) Int. Cl.$^7$ .............................................. G01N 21/00
(52) U.S. Cl. ................. 356/237.1; 356/237.1; 356/237.2; 356/237.3
(58) Field of Search ..................... 356/237.1, 394, 356/237, 237.2; 359/390, 392; 350/87; 355/30; 382/108

(56) References Cited

U.S. PATENT DOCUMENTS

| | | | | |
|---|---|---|---|---|
| 4,148,552 A | * | 4/1979 | Suzuki et al. ................ 359/388 |
| 4,537,509 A | * | 8/1985 | Kronfeld ...................... 33/276 |
| 4,801,977 A | * | 1/1989 | Ishizaka et al. ............... 355/30 |
| 5,140,643 A | * | 8/1992 | Izumi et al. .................. 348/87 |
| 5,175,644 A | * | 12/1992 | Dosaka ........................ 359/368 |
| 5,563,703 A | * | 10/1996 | Lebeau et al. ............... 348/126 |
| 5,909,285 A | * | 6/1999 | Beaty et al. ................. 348/126 |
| 5,940,174 A | * | 8/1999 | Mueller et al. .......... 250/201.5 |
| 6,094,263 A | * | 7/2000 | Tomiya et al. ........... 356/237.1 |
| 6,160,662 A | * | 12/2000 | Uchida et al. ............... 359/368 |

* cited by examiner

Primary Examiner—Michael G. Lee
Assistant Examiner—Kumiko C. Koyama
(74) Attorney, Agent, or Firm—Ronald Feece; Bracewell & Patterson, L.L.P.

(57) ABSTRACT

A jig for inspecting the appearance of small parts with an optical microscope, the jig is equipped with a base, having an upper flat surface which becomes a mounting stage of the optical microscope, and is also provided with a member for moving the upper flat surface at least in a direction approximately parallel to a direction of an optical axis of an objective lens of the optical microscope in order to focus the optical microscope on an inspection portion of the small parts mounted on the upper flat surface. The jig is also equipped with an inspection-object supporting portion, provided with a member for supporting the small parts at the predetermined portion on the base. Furthermore, the jig is equipped with reflecting mirrors which have a mirrorlike surface with an inclined angle of approximately 45 degrees to the upper flat surface of the base.

19 Claims, 16 Drawing Sheets

Visual field of optical microscope

APPEARANCE INSPECTING JIG FOR SMALL PARTS AND INSPECTING METHOD EMPLOYING THE SAME JIG

This application claims priority to Japanese Patent No. JP 2000-200861 (IBM Docket No. JP920000147JP1, filed on Jul. 3, 2000, and entitled "Appearance Inspecting Jig For Small Parts and Inspecting Method Employing the Same Jig."

BACKGROUND OF THE INVENTION

1. Technical Field

The present invention relates to an inspecting jig and an inspecting method that are used in inspecting the appearance of small parts, such as a head assembly, by use of an optical microscope, and more particularly to an inspecting jig and an inspecting method which enable an inspector to inspect many faces of small parts during a single holding operation.

2. Description of the Related Art

A conventional method of inspecting the appearance of small parts, such as a head assembly, by use of an optical microscope will hereinafter be described.

FIG. 18 shows a perspective view of a conventional appearance inspecting method for head assemblies, and FIG. 19 is a diagram showing the image of the visual field of an optical microscope in the conventional appearance inspecting method for head assemblies.

In FIG. 18, reference numeral 103 denotes an objective lens of an optical microscope, 30 a head assembly which is small parts, 150 an empty hand or inspecting glove, and "PU" the upper-face image of the head assembly. An appearance inspector for head assemblies inspects the appearance of the head assembly 30 by inspecting the upper-face image PU (see FIG. 19) of the head assembly 30 obtained through the objective lens 103.

FIG. 19 is a diagram showing the image of the visual field of the optical microscope obtained by carrying out the inspection shown in FIG. 18. Reference numeral 31 denotes left wiring, 32 denotes right wiring, 33 denotes a head, 34 denotes a left connecting portion between the left wiring 31 and the head 33, 35 denotes a right connecting portion between the right wiring 32 and the head 33, and 36 denotes a load beam portion.

In the head assembly 30 shown in FIGS. 18 and 19, appearance inspection is unnecessary for the lower face of the head assembly 30, because the wiring 31 and the wiring 32 are in intimate contact on the side of the head 33 of the load beam portion 36. However, there is a need to inspect the connected states of the left and right connecting portions 34, 35 and to inspect the state of the intimate contact of the left and right wirings 31, 32 on the load beam portion 36.

For inspecting the connected states of the left and right connecting portions 34, 35, the direction of the upper-face image PU shown in FIG. 19 is insufficient. The appearance inspector must change, for example, the direction of the head assembly 30 so that as many portions of the connecting portions 34, 35 as possible are visible. More specifically, the appearance inspector has to change the direction of the head assembly 30 so that as many portions of the connecting portions 34, 35 as possible are at the focal position (within the focal depth) of the optical microscope and also on a plane perpendicular to the optical axis of the objective lens 103. In the event the position of the head assembly 30 is improper when inspecting the upper-face image PU, the appearance inspector has to change the position of the head assembly 30.

The direction of the upper-face image PU shown in FIG. 19 is also insufficient in the case of inspecting the state of the intimate contact of the left and right wirings 31, 32 on the load beam portion 36. The appearance inspector must change, for example, the direction of the head assembly 30 so that as many portions of the left and right wirings 31, 32 and the load beam portion 36 as possible are visible. More specifically, the appearance inspector has to inspect the state of the intimate contact of the left wiring 31, by changing the direction of the head assembly 30 so that the entire left wiring 31 is at the focal position (within the focal depth) of the optical microscope and also on a plane perpendicular to the optical axis of the objective lens 103. Then, the appearance inspector has to inspect the state of the intimate contact of the right wiring 32, by changing the direction of the head assembly 30 so that the entire right wiring 32 on the opposite side is on a plane perpendicular to the optical axis of the objective lens 103. In the case where the position of the head assembly 30 is improper at the time of inspecting the upper-face image PU, the appearance inspector has to change the position of the head assembly 30 at the time of inspecting the left wiring 31, and at the time of inspecting the right wiring 32.

In addition, since the head assembly 30 is so small that an optical microscope is required at the time of inspecting the connecting portions and wiring state, it is difficult to execute a suitable holding method wherein the upper-face image PU is inspected in raising the head assembly 30 with an empty hand or inspecting glove 150, then the connecting portions 34, 35 are changed to the direction of inspection, and furthermore, the directions of the left and right wirings 31, 32 are also changed so that they can be inspected.

As described supra, the appearance inspector for the head assembly 30 has to change many times the position of the head assembly 30 in order to inspect the connected states of the left and right connecting portions 34, 35 or the states of the intimate contact of the left and right wirings 31, 32 on the load beam portion 36. Furthermore, the focal point of the microscope must coincide with a position of inspection and each time the holding position is changed.

In the conventional method of inspecting the head assembly 30, as stated above, the appearance inspector for the head assembly 30 inspects the upper face of the head assembly 30, the connected states of the left and right connecting portions 34, 35; and the left and right wirings 31, 32, by changing many times the position of the main body (load beam portion) of the head assembly 30, with the empty hand or the inspecting glove 150, etc., so that the inspection portions of the head assembly 30 are as perpendicular as possible to the optical axis of the objective lens 103, and so that the inspection portions coincide with the focal point of the microscope.

In the above-mentioned conventional appearance inspection of the head assembly 30, however, there is a problem that there are instances where (1) during inspection, the head assembly 30 and the objective lens 103 contact and are damaged, and (2) the static electricity stored in the body of the inspector destroys the head assembly 30 or causes dirt to adhere to the head assembly 30, resulting in a reduction in the quality of the head assembly 30.

The present invention has been achieved in order to solve the aforementioned conventional problems. Accordingly, it is the primary object of the present invention to provide a jig and a method which eliminate the need for the inspector to change many times the position of the head assembly 30 at the time of making an appearance inspection in many directions.

Thus, according to the present invention, when carrying out the appearance inspection in many directions, only a series of operations for gradually raising the universal focus-adjusting lever upward are required, after the inspector first brings the upper-face image of the head assembly into focus with the focus adjusting handle. Therefore, the inspector can readily inspect the right side face, left side face, and front face of the head assembly without changing many times the position of the head assembly.

In addition, the present invention is capable of preventing damage due to the contact between the head assembly and objective lens in the course of inspection, destruction of the head assembly due to static electricity stored in the inspector's body, and a reduction in the quality due to dirt on the head assembly, because the inspector does not directly hold the head assembly.

Furthermore, the present invention is capable of readily inspecting the lower face of the head assembly in addition to the right side face, left side face, and front face, by carrying out a series of operations for gradually raising the universal focus-adjusting lever upward, after the inspector first brings the upper-face image of the head assembly into focus with the focus adjusting handle.

Finally, the present invention is capable of easily inspecting the upper, right, left, and lower faces of the head assembly and also efficiently performing the operation of inspecting a plurality of head assemblies, because the inspector can set a plurality of head assemblies on the appearance inspecting jig at one time.

SUMMARY OF THE INVENTION

To attain the above-mentioned object, a jig is provided for inspecting the appearance of small parts with an optical microscope, comprising (1) a base, having an upper flat surface which becomes a mounting stage of the optical microscope, and also provided with a member for moving the upper flat surface at least in a direction approximately parallel to a direction of an optical axis of an objective lens of the optical microscope in order to focus the optical microscope on an inspection portion of the small parts mounted on the upper flat surface; and (2) an inspection-object supporting portion, provided with a member for supporting the small parts, which is mounted on the upper flat surface. The inspection-object supporting portion is provided with at least one reflecting mirror which has a mirrorlike surface with an inclined angle of approximately 45 degrees to the upper flat surface, the reflecting mirror being disposed on the inspection-object supporting portion in such a manner that the mirrorlike surface is positioned, facing one side face of the small parts so that an image of the one side face is reflected at the mirrorlike surface and visible within a visual field of the optical microscope.

The inspecting method of employing an appearance inspecting jig of the present invention is a method of inspecting the appearance of small parts with an optical microscope employing an appearance inspecting jig which comprises: a base, having an upper flat surface which becomes a mounting stage of the optical microscope, and also provided with a member for moving the upper flat surface so that the optical microscope is focused at a position of inspection of the small parts mounted on the upper flat surface; and an inspection-object supporting portion, provided with a member for supporting the small parts, which is mounted on the upper flat surface; the inspection-object supporting portion being provided with a reflecting mirror which has a mirrorlike surface with an inclined angle of approximately 45 degrees to the upper flat surface, the reflecting mirror being disposed so that at least one side face of the small parts and the mirrorlike surface of the reflecting mirror face each other. The method comprises the steps of: making an inspection with an upper face of the small parts moved to a focal position of the optical microscope, by employing the moving member; and inspecting the at least one side face of the small parts projected on the mirrorlike surface of the reflecting mirror, by employing the moving means.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

DETAILED DESCRIPTION OF THE PREFERRED EMBODIMENT

Before describing an appearance inspecting jig of the present invention and an inspecting method employing the jig, a description will be given of a head assembly which is an inspection object requiring appearance inspection.

Figure 1:
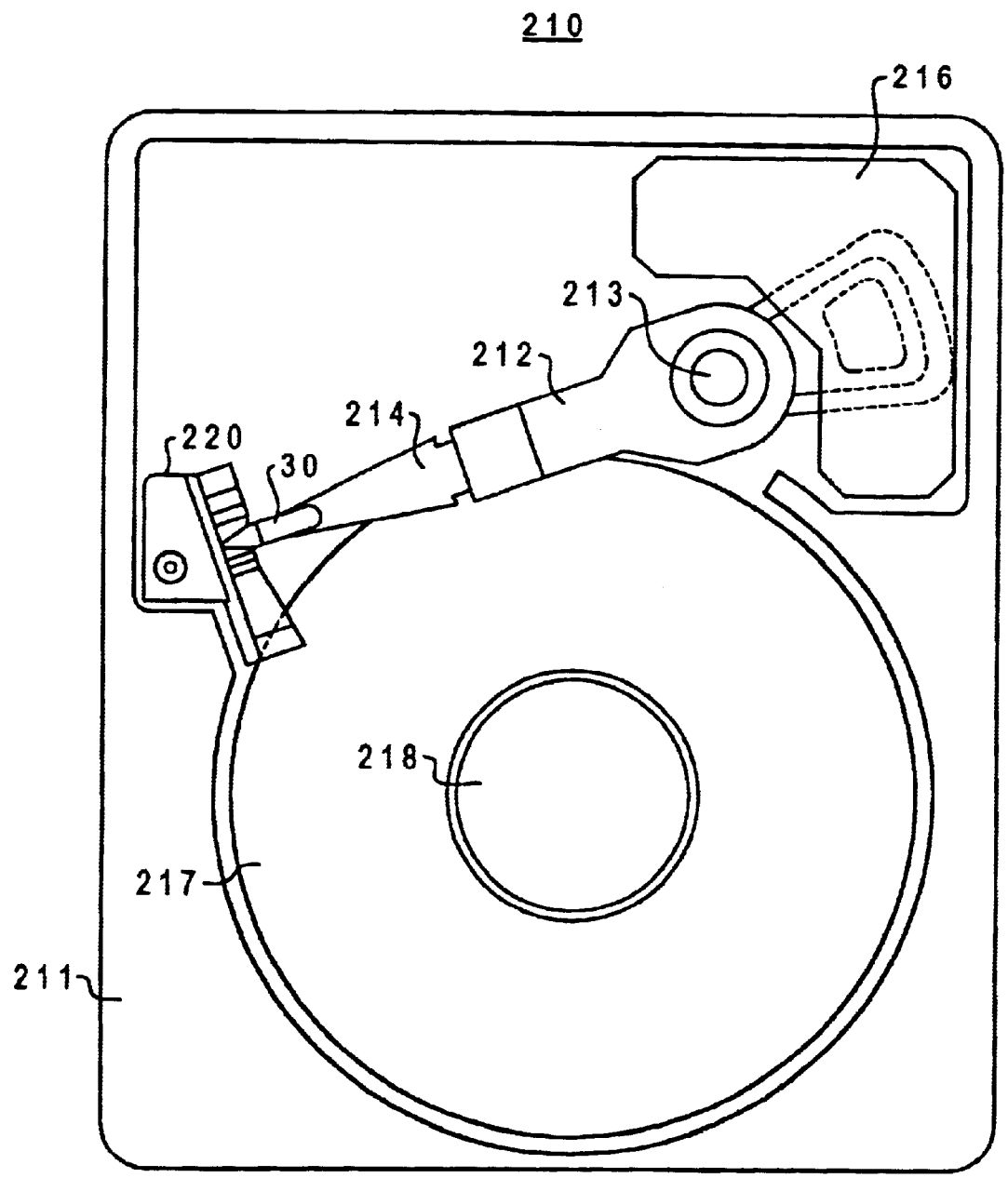
FIG. 1 is a plan view of a magnetic recording disk unit in which a head assembly to be inspected by a first embodiment is employed.

FIG. 1 is a plan view of a magnetic recording disk unit in which a head assembly to be inspected in this embodiment is employed.

The magnetic recording disk unit 210 of FIG. 1 houses a recording disk 217, a rotary actuator assembly 212, a voice coil motor 216, and a ramp 220 into a housing 211 and forms an airtight space in the inside. For the recording disk 217, a plurality of disks, each provided on the upper and lower surfaces with a magnetic recording layer, are stacked and rigidly attached to a spindle shaft 218. Each disk is rotated along with the spindle shaft 218 by a spindle motor (not shown). The upper and lower surfaces of each of the recording disks 217 are each used as an information-recording surface, and a dedicated magnetic head (not shown) is employed for each surface. For the actuator assembly 212, suspension arms 214 corresponding in number to the information-recording surfaces are stacked and supported on a pivot shaft 213. A head assembly 30, equipped with a magnetic head for scanning the upper and lower information-recording surfaces of each disk, is attached to the point end portion of the each suspension arm 214.

The actuator assembly 212 rotates on the pivot shaft 213 by the voice coil motor 216, thereby loading the head assembly 30, equipped with the magnetic head, over each disk surface or unloading the head assembly 30 to the ramp 220. The suspension arm 214 is formed from elastic material and urged in the direction in which each head assembly 30 attached to each arm approaches the corresponding disk surface of the recording disks 217. If the force of floating the head assembly 30, developed by rotation of the recording disk 22, is balanced with the elastic force of the suspension arm 214, the head assembly 30 will float off the recording disk 217 being rotated, while maintaining a constant distance from the disk surface.

As described above, the head assembly 30 that is inspected by this embodiment is a component that is employed within the magnetic recording disk unit 210, and there is an ever-increasing demand for a reduction in size and an increase in capacity of the magnetic recording disk unit itself. Therefore, the head assembly 30, is which is originally a very small precision component, has been desired to be of smaller size and more precise. In the small precision head assembly 30, it is difficult to visually inspect the connection, etc., between the magnetic head and wiring by the naked eye. Hence, before assembling the head assembly 30 into the magnetic disk unit, as described in the prior art, the inspector performs inspection, such as inspection of whether the magnetic head and the wiring have securely been connected and inspection of whether the wiring is in intimate contact with the main body (load beam portion) of the head assembly 30 without touching a disk surface, etc., by use of an optical microscope (or a stereomicroscope).

Figure 2:
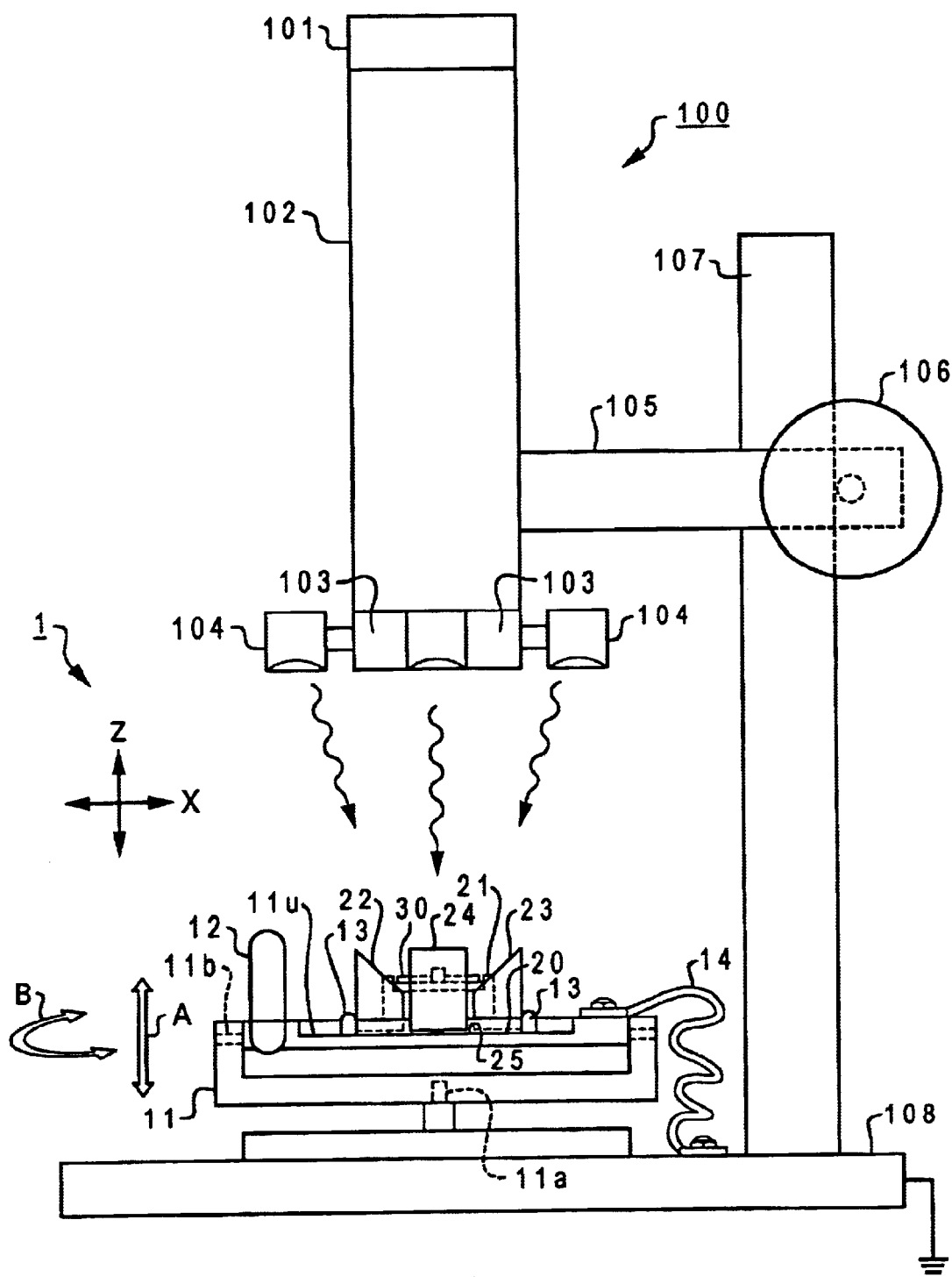
FIG. 2 is a side elevational view showing an appearance inspecting jig of a the first embodiment of the present invention set in the optical microscope.
Figure 3:
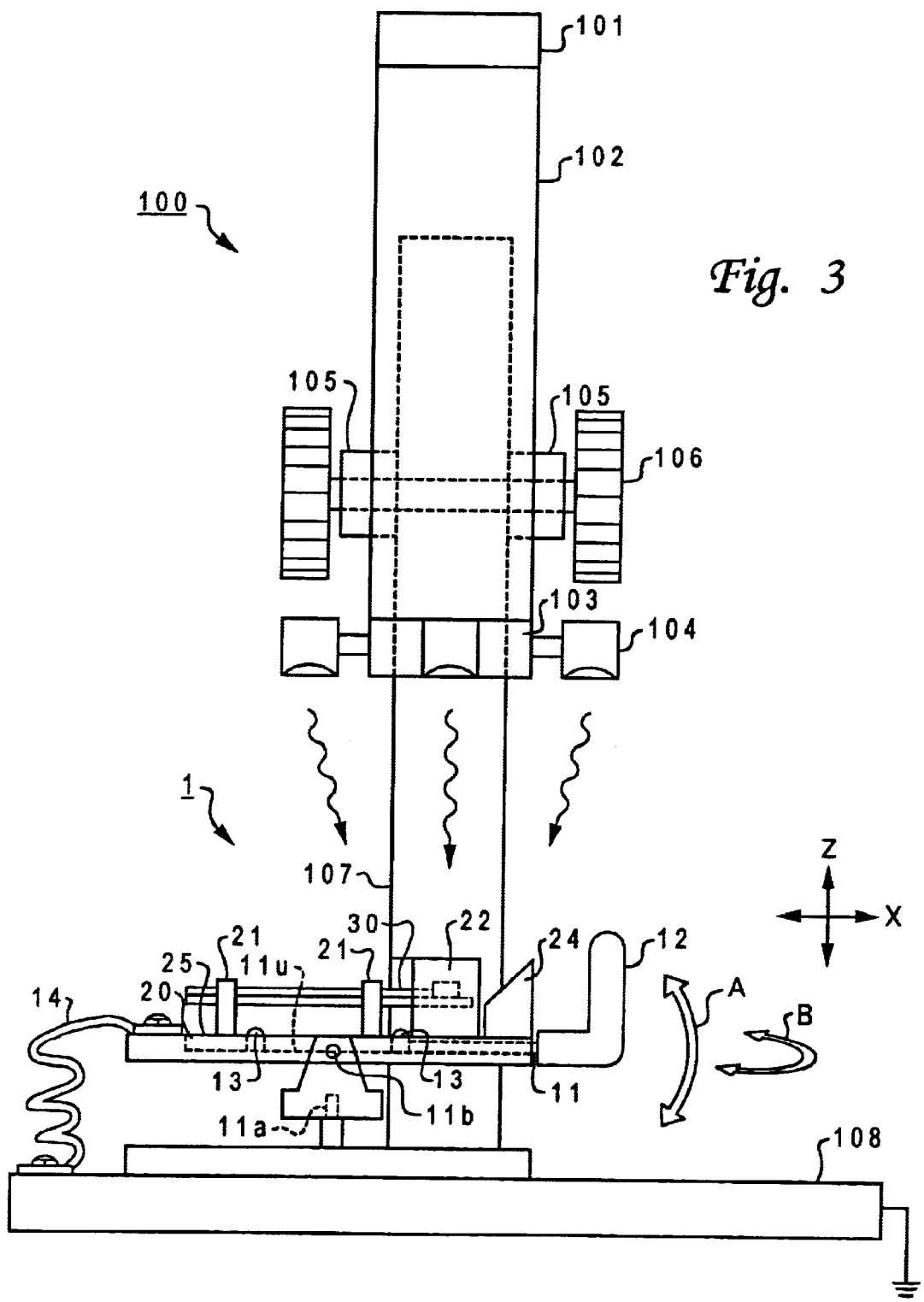
FIG. 3 shows a front elevational view of the optical microscope and appearance inspecting jig of FIG. 2.

FIG. 2 is a side elevational view showing the appearance inspecting jig of the first embodiment of the present invention set in the optical microscope; FIG. 3 shows a front elevational view of the optical microscope and the appearance inspecting jig of FIG. 2.

As illustrated in FIGS. 2 and 3, the appearance inspecting jig 1 of the first embodiment is used in combination with the optical microscope 100 so that the upper flat surface 11u of the jig 1 is located at the position of a mounting stage.

The optical microscope 100 is configured by an ocular lens 101 through which the inspector views; a lens barrel 102 for preventing the entrance of external light, while keeping the parallelism between the ocular lens 101 and an objective lens 103 to be described later and also supporting both lenses; the objective lens 103 installed to face the surface of an inspection object to be inspected; an illuminator 104 for illuminating the inspection object; a lens-barrel supporting portion 105 for fixing the lens barrel 102 over the inspection object; a focus adjusting handle 106 for moving the lens-barrel supporting 105 up and down by a dial handle to adjust focus; a pillar 107 to which the lens-barrel supporting portion 105 is attached; and a pillar stand 108 in which the pillar 107 is stood up to be grounded.

While the optical microscope 100 of FIG. 2 has been illustrated as a microscope for a single eye, it may be a stereomicroscope for both eyes. Also, although the lens-barrel supporting portion 105, focus adjusting handle 106, pillar 107, pillar stand 108, etc., have been illustrated in FIGS. 2 and 3 as the simplest form to explain their functions, they may be in another form. In addition, although four (4) illuminators 104 have been illustrated in FIGS. 2 and 3, one or more illuminators may be employed as the case may be, when natural light is insufficient. For instance, a single ring-shaped illuminator may be employed. The number and shape of illuminators may also be arbitrarily selected, depending on the peripheral brightness state and the illuminating power of each illuminator 104.

The appearance inspecting jig 1 is composed of a base (universal base) 11 which is capable of moving the conductive upper flat surface 11u, which becomes a mounting stage, in both a vertical direction approximately parallel to the optical axis of the objective lens 103 of the microscope 100 and a horizontal direction which forms the same plane as the upper flat surface 11u, and an inspection-object supporting portion 20 for supporting the head assembly 30 which is an inspection object.

The universal base 11 will hereinafter be described in further detail.

Figure 4:
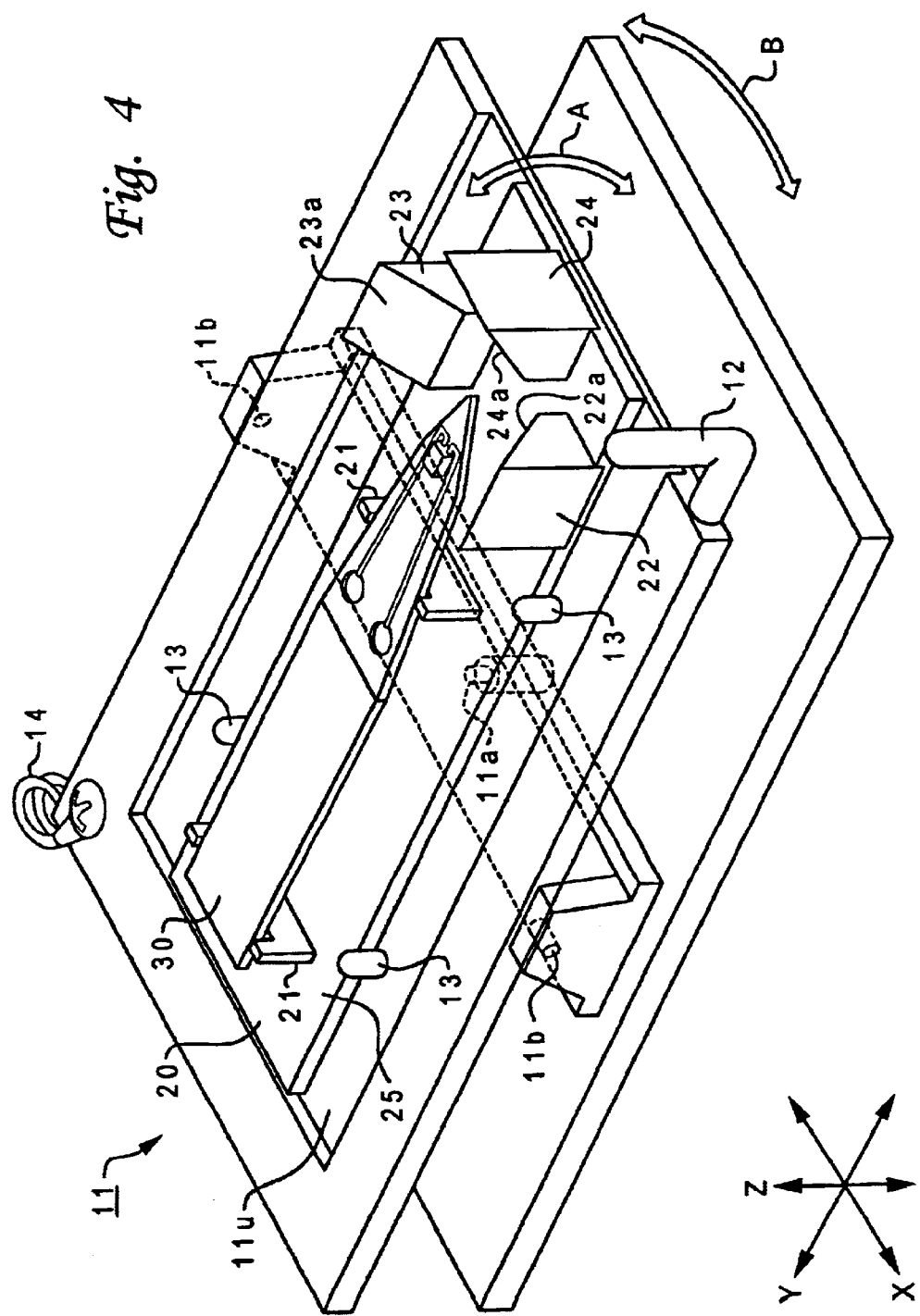
FIG. 4 is a perspective view showing in detail the universal base 11 shown in FIGS. 2 and 3.

FIG. 4 is a perspective view showing in detail the universal base 11 shown in FIGS. 2 and 3.

As illustrated in FIG. 4, the universal base 11 has a horizontal rotating shaft 11a provided perpendicularly to an X-Y plane (which includes the upper flat surface 11u which becomes a mounting stage) so that the upper flat surface 11u can move along the X-Y plane in a direction of an arrow B; a vertical rotating shaft 11b which can move the upper flat surface 11u, which becomes a mounting stage, in a direction of an arrow A approximately parallel to the optical-axis direction of the objective lens 103 of the optical microscope 100; a universal focus-adjusting lever 12 as an assisting means which can easily move the upper flat surface 11u in both the direction of the arrow A and the direction of the arrow B; a positioning pin 13 that is positioning means which can detachably fix the inspection-object supporting portion 20 on the upper flat surface 11u of the universal base 11; and an earth line 14 for escaping static electricity from the conductive upper flat surface 11u of the universal base 11 to the pillar stand 108.

With the configuration of the rotating shafts 11a, 11b of the universal base 11, the inspector can easily move each inspection portion of the head assembly 30 so that it is brought into focus. The moving means, however, does not need to be the aforementioned rotating shafts 11a, 11b, but may be a sliding mechanism, etc. Although not shown, for example, an X-Y sliding mechanism consisting of a combination of guide pins and rails for movement in the X-direction and Y-direction may be provided on the bottom surface of the universal base 11. With the X-Y sliding mechanism, the universal base 11 can freely move parallel along the X-Y plane. In addition, bearings, etc., may be added to the above-mentioned guide pins to reduce the force required for parallel movement along the X-Y plane. With the bearings, etc., it can more freely move. Thus, by enhancing the degree of freedom of the universal base 11 on the X-Y plane, a portion of the head assembly 30 to be inspected can be readily moved within the visual field of the optical microscope 100.

The static electricity stored in the body of the inspector is transmitted, for example, from the universal focus-adjusting lever 12 through the conductive upper flat surface 11u to the earth line 14, and furthermore, the earth line 14 is connected to the pillar stand 108 connected to ground. Therefore, the static electricity finally flows into ground. Thus, in this embodiment, there is no possibility that the static electricity stored in the inspector's body will flow in the head assembly 30 and destroy it.

The inspection-object supporting portion 20 is placed on the upper flat surface 11u of the universal base 11, and consists of (1) supporting legs 21 (supporting means) for supporting (fixing) the head assembly 30 which is an inspection object; (2) a right mirror block 22 (reflecting means), equipped with a right mirrorlike surface 22a having an inclined angle of approximately 45 degrees to the upper flat surface 11u of the universal base 11, and placed so that the right mirrorlike surface 22a guides the right side-face image of the head assembly 30 to the objective lens 103 of the microscope 100; (3) a left mirror block 23 (reflecting means), having a left mirrorlike surface 23a with an inclined angle of approximately 45 degrees, as with the above-mentioned right mirror block 22, and placed so that the left mirrorlike surface 23a guides the left side-face image of the head assembly 30 to the objective lens 103 of the microscope 100; (4) a front mirror block 24 (reflecting means), having a front mirrorlike surface 24a with an inclined angle of approximately 45 degrees, as with the right and left mirror blocks 22 and 23, and placed so that the front mirrorlike surface 24a guides the front-face image of the head assembly 30 to the objective lens 103 of the microscope 100; and (5) a conductive base plate 25 as a base for placing the above-mentioned supporting legs 21 and mirror blocks 22 to 24. The mirror blocks 22 to 24 will be described later with FIG. 6.

The inspection-object supporting portion 20 will hereinafter be described in further detail.

Figure 5:
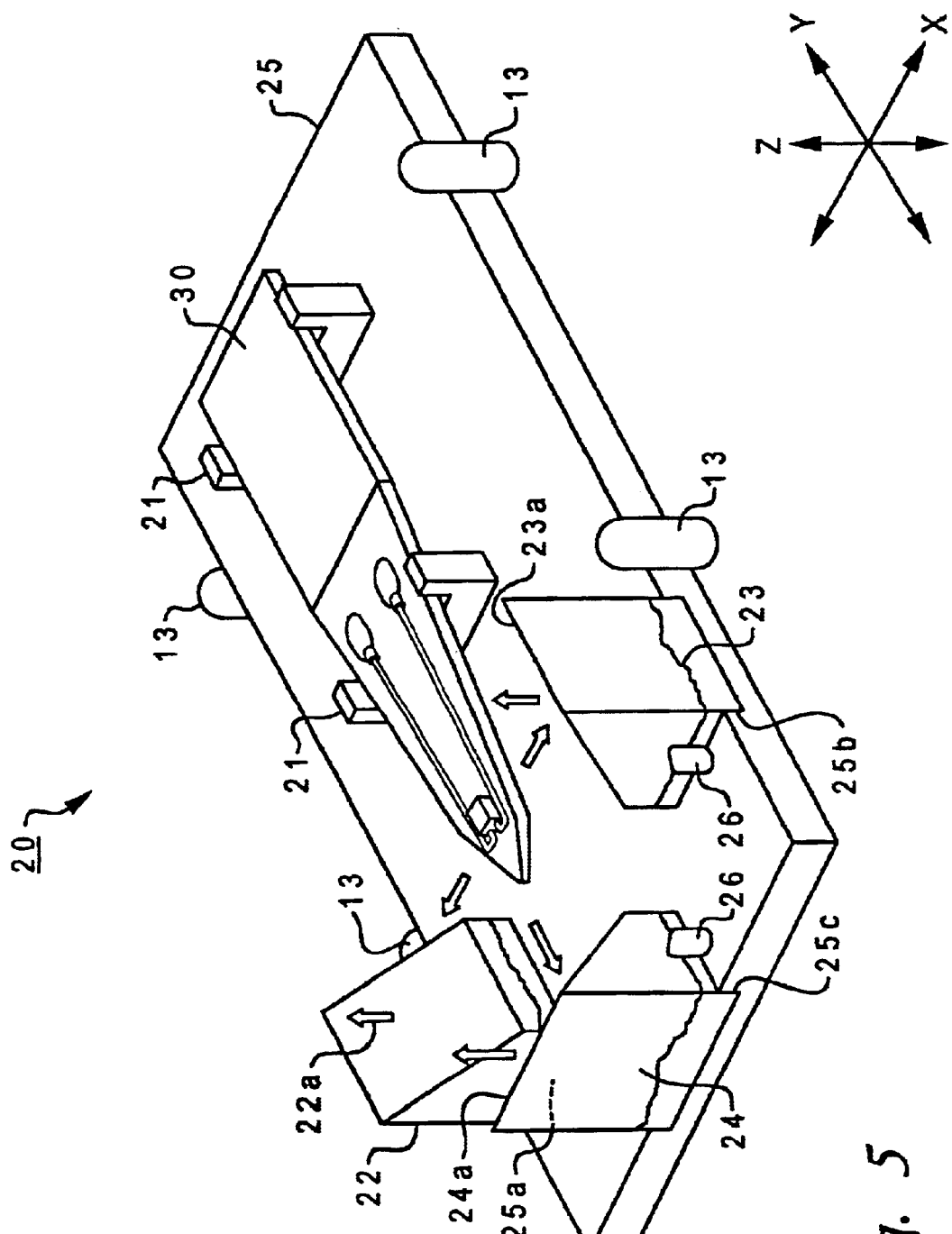
FIG. 5 is a perspective view showing in detail the inspection-object supporting portion shown in FIGS. 2 and 3.

FIG. 5 is a perspective view showing in detail the inspection-object supporting portion 20 shown in FIGS. 2 and 3.

As illustrated in FIG. 5, recesses 25a to 25c, having the same dimension as the bottom surface of each of the mirror blocks 22 to 24, are provided on the base plate 25 to fix the mirror blocks 22 to 24 at predetermined positions. The right mirror block 22 is fitted into the recess 25a on the base plate 25, with the right mirrorlike surface 22a positioned in front of the right side face of the head assembly 30 so that the image of the right side face of the head assembly 30 is guided to the objective lens 103 of the microscope 100. Similarly, the left mirror block 23 is fitted into the recess 25b on the base plate 25, with the left mirrorlike surface 23a positioned in front of the left side face of the head assembly 30 so that the image of the left side face of the head assembly 30 is guided to the objective lens 103 of the microscope 100. The front mirror block 24 is fitted into the recess 25c on the base plate 25 with the front mirrorlike surface 24a positioned in front of the head assembly 30 so that the image of the front face of the head assembly 30 is guided to the objective lens 103 of the microscope 100. In addition, the fitted mirror blocks 22 to 24 and the base plate 25 are more firmly fixed and electrically connected by a conductive adhesive 26.

Therefore, even when the mirror blocks 22 to 24 are charged with static electricity, it is transmitted, for example, from the base plate 25 through the conductive upper flat surface 11u to the earth line 14. Furthermore, since the earth line 14 is connected to the pillar stand 108 connected to ground, the static electricity finally flows into ground. In this manner, the destruction of the head assembly 30 due to current flowing in the head assembly 30 can be prevented.

Now, the configuration of the mirror blocks 22 to 24 will be described in further detail.

FIG. 6 is a diagram showing a configuration example of each mirror block shown in FIG. 5.

Figure 6A:
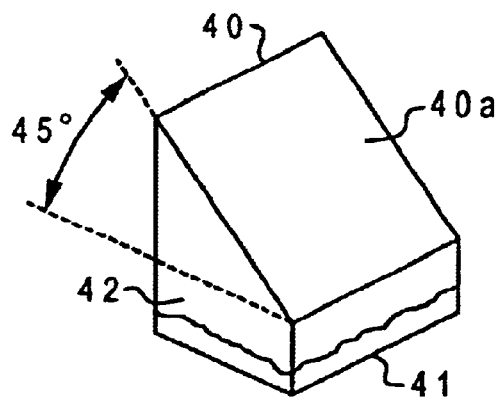
FIGS. 6A, B, and C are diagrams showing a configuration example of each mirror block shown in FIG. 5.

A mirror block 40 shown in FIG. 6A has a shape chamfering one side of an optical glass block in the form of a rectangular solid at an angle of approximately 45 degrees from that block. When the chamfered surface (inclined surface) is placed upward, it has an inclined angle of approximately 45 degrees with respect to the bottom surface. As the mirror block 40 is provided on the base plate 25, and the base plate 25 is disposed on the upper flat surface 11u of the universal base 11, the inclined surface of the mirror block 40 has an inclined angle of approximately 45 degrees with respect to the upper flat surface 11u.

The mirror block 40, as stated above, is configured by a glass block having a bottom surface and an inclined surface of approximately 45 degrees, and a film 42 deposited uniformly on the surface of the glass block 41, including the inclined surface, to finish the surface like a mirror. Because the deposited film 42 is formed on the inclined surface of the glass block 41, the inclined surface becomes a mirrorlike surface 40a which changes the direction of horizontal incident light and reflects it upward at a right angle. The glass block 41 has no conductivity, while the deposited film 42 has conductivity. Therefore, the static electricity stored in the block mirror 40 can escape to the earth line 14, by connecting the deposited film 42 with the conductive base plate 25, or by electrically connecting the deposited film 42 and the base plate 25 by the conductive adhesive 26. Thus, in the case of employing this mirror block 40, destruction of devices on the head assembly 30, etc., due to static electricity will no longer occur.

Figure 6B:
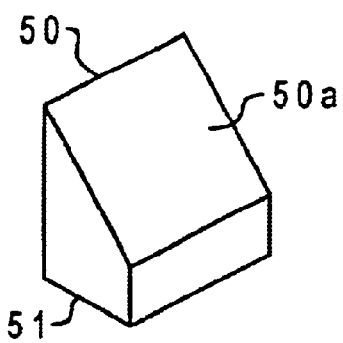

A mirror block 50 shown in FIG. 6B comprises a metal block 51 in the form chamfering one side of a conductive, rectangular metal block at an angle of approximately 45 degrees from the conductive metal block. When the chamfered surface (inclined surface) is placed upward, it has an inclined angle of approximately 45 degrees with respect to the bottom surface. The inclined surface of the metal block 51 becomes a mirrorlike surface 50a, which changes the direction of horizontal incident light and reflects it upward at a right angle, by finishing the inclined surface like a mirror by mechanical or chemical processing.

Figure 6C:
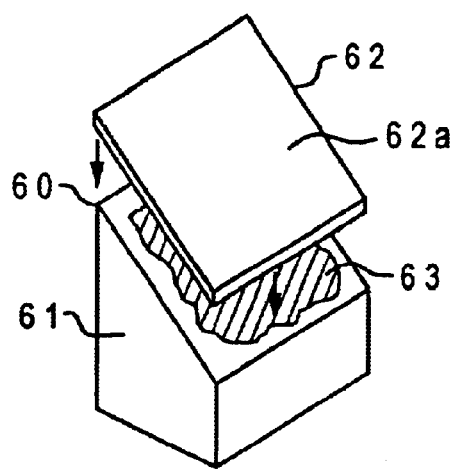

A mirror block 60 shown in FIG. 6C is made up of a metal block 61 in the form chamfering one side of a conductive, rectangular metal block at an angle of approximately 45 degrees from the conductive metal block, and a mirrorlike sheet 62 having one surface finished like a mirror. The mirrorlike sheet 62 is glued to the chamfered surface (inclined surface) of the metal block 61 by a conductive adhesive 63, etc. The exposed surface of the glued mirrorlike surface 62 serves as a mirrorlike surface 62a which changes the direction of horizontal incident light and reflects it upward at a right angle, because the exposed surface has been finished like a mirror.

While it has been described and illustrated in FIG. 5 that the mirror blocks 22 to 24, fitted into the base plate 25, and the base plate 25 are rigidly fixed and electrically connected by the conductive adhesive 26, the fixing and electrical conduction between the mirror blocks 22 to 24 and the base plate 25 can be performed by a means differing from the conductive adhesive 26.

Figure 7:
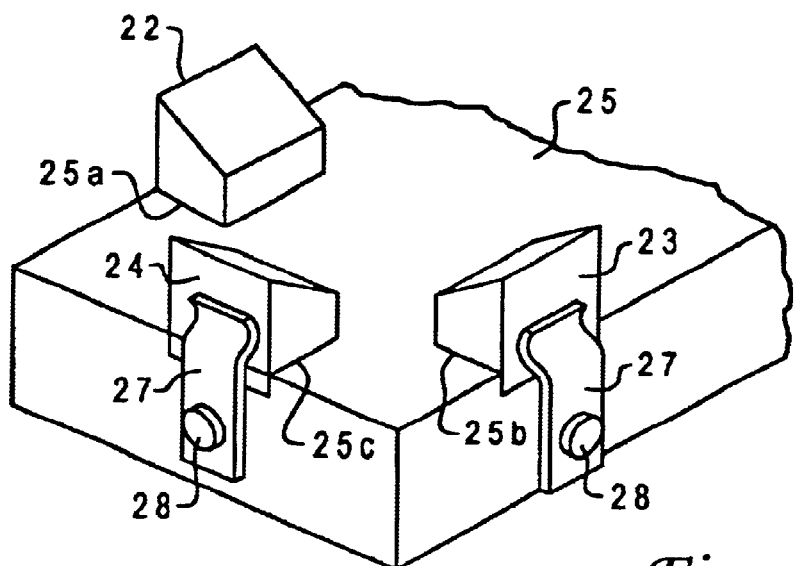
FIG. 7 is a perspective view showing another example in which mirror blocks are fixed to a base plate.

FIG. 7 is a perspective view showing another example in which the mirror blocks 22 to 24 are fixed and electrically connected to the base plate 25.

FIG. 7 is similar to FIG. 5 in that the mirror blocks 22 to 24 are fitted into the recesses 25a to 25c of the base plate 25 but differs in that the mirror blocks 22 to 24 are urged toward the recesses 25a to 25c by plate spring members 27, formed from elastic metal, which are fixed to the base plate 25 by means of screws 28. Therefore, even when configured as shown in FIG. 7, the mirror blocks 22 to 24 are fixed and electrically connected to the base plate 25.

In addition, employing the plate spring members 27 to fix the mirror blocks 22 to 24 to the base plate 25 can facilitate, for example, the operation of exchanging a mirror block damaged.

Now, a description will be made of the fact that by disposing the mirror blocks 22 to 24 around the head assembly 30 which is an inspection object, as shown in FIG. 5, a right side-face image PR, which is an image reflected from the right side face of the head assembly 30, a left side-face image PL, which is an image reflected from the left side face of the head assembly 30, and a front-face image PF, which is an image reflected from the front face of the head assembly 30, as well as an upper-face image PU which is an image reflected from the upper face of the head assembly 30 illuminated by the illuminator 104, can be guided so that they are all incident on the objective lens 103.

Figure 8:
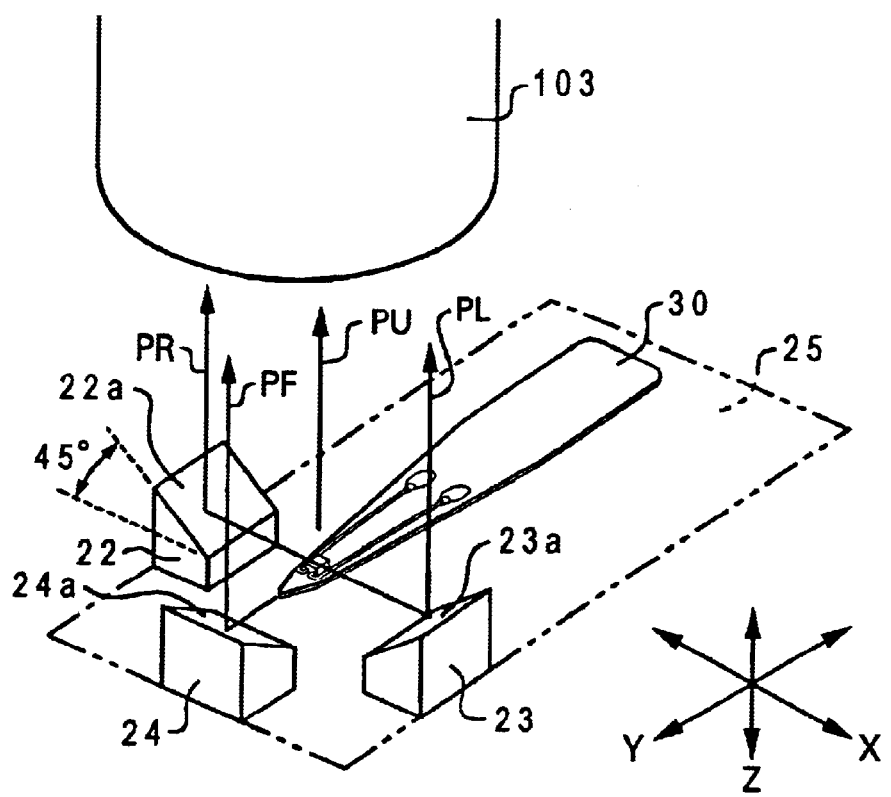
FIG. 8 is a diagram showing the path of the image of each face of the head assembly.

FIG. 8 is a diagram showing the path of the image of each face of the head assembly 30.

Figure 18:
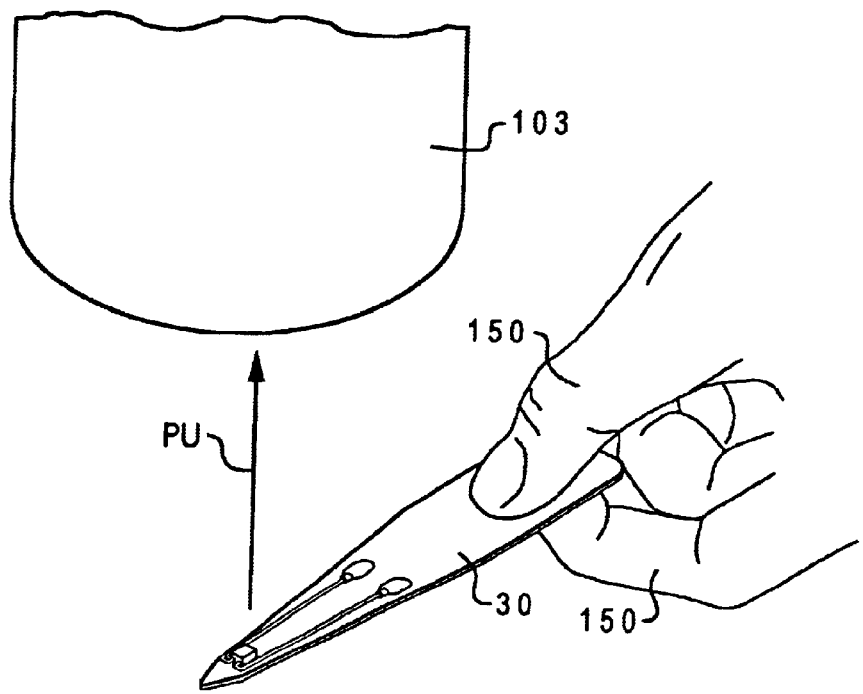
FIG. 18 is a perspective view of a conventional appearance inspecting method for head assemblies.
Figure 19:
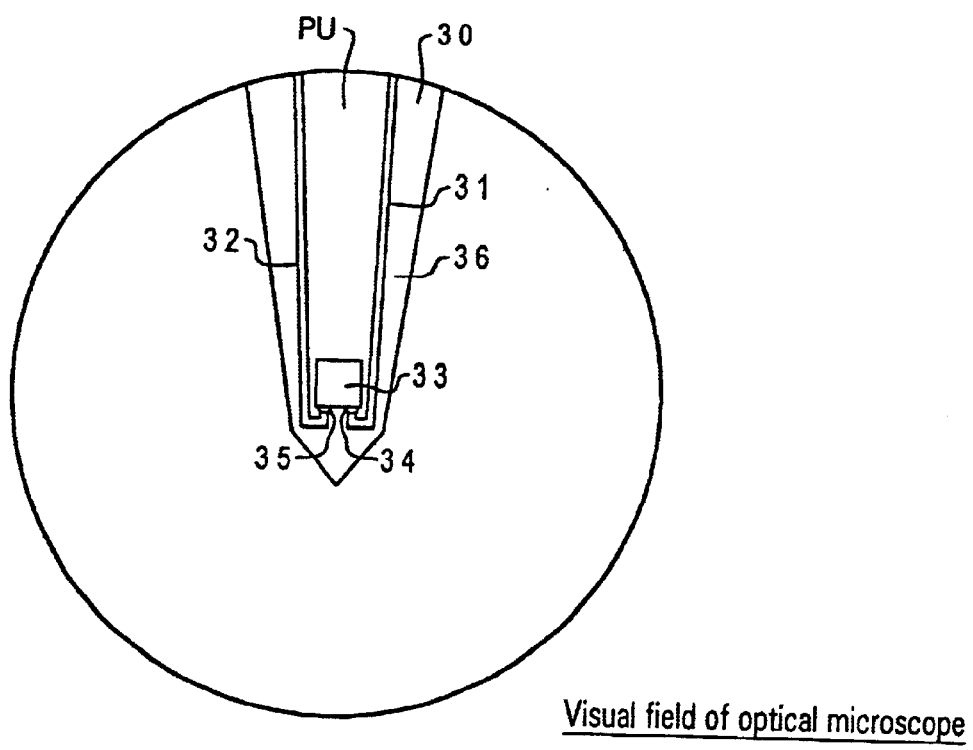
FIG. 19 is a diagram showing the image of the visual field of an optical microscope in the conventional appearance inspecting method for head assemblies.

For the upper-face image PU of the head assembly 30, as with the conventional inspection shown in FIGS. 18 and 19, the light irradiated from the illuminator 104 is reflected at the upper face of the head assembly 30 and incident directly on the objective lens 103. For the right side-face image PR of the head assembly 30, the light from the right side face of the head assembly 30 is reflected upward at a right angle by the right mirrorlike surface 22a of the right mirror block 22 and incident on the objective lens 103. For the left side-face image PL of the head assembly 30, the light from the left side face of the head assembly 30 is reflected upward at a right angle by the left mirrorlike surface 23a of the left mirror block 23 and incident on the objective lens 103. For the front-face image PF of the head assembly 30, the light from the front face of the head assembly 30 is reflected upward at a right angle by the front mirrorlike surface 24a of the front mirror block 24 and incident on the objective lens 103.

Incidentally, as clear from the length of an arrow representing the path of each image of the head assembly 30 of FIG. 8, the path lengths along which the right side-face image PR, left side-face image PL, and front-face image PF of the head assembly 30 are incident on the objective lens 103 are longer than the path length along which the upper-face image PU is incident on the objective lens 103. Therefore, if the upper-face image PU of the head assembly 30 is brought into focus, then the right side-face image PR, left side-face image PL, and front-face image PF will be out of focus.

Hence, in the first embodiment, the inspector moves the inspection-object supporting portion 20 on the universal base 11 by operating the above-mentioned universal focus-adjusting lever 12, and can readily view each side-face image or the front-face image, following the upper-face image PU of the head assembly 30, without operating the focus adjusting handle 106 each time the focus adjusting lever 12 is operated.

Figure 9:
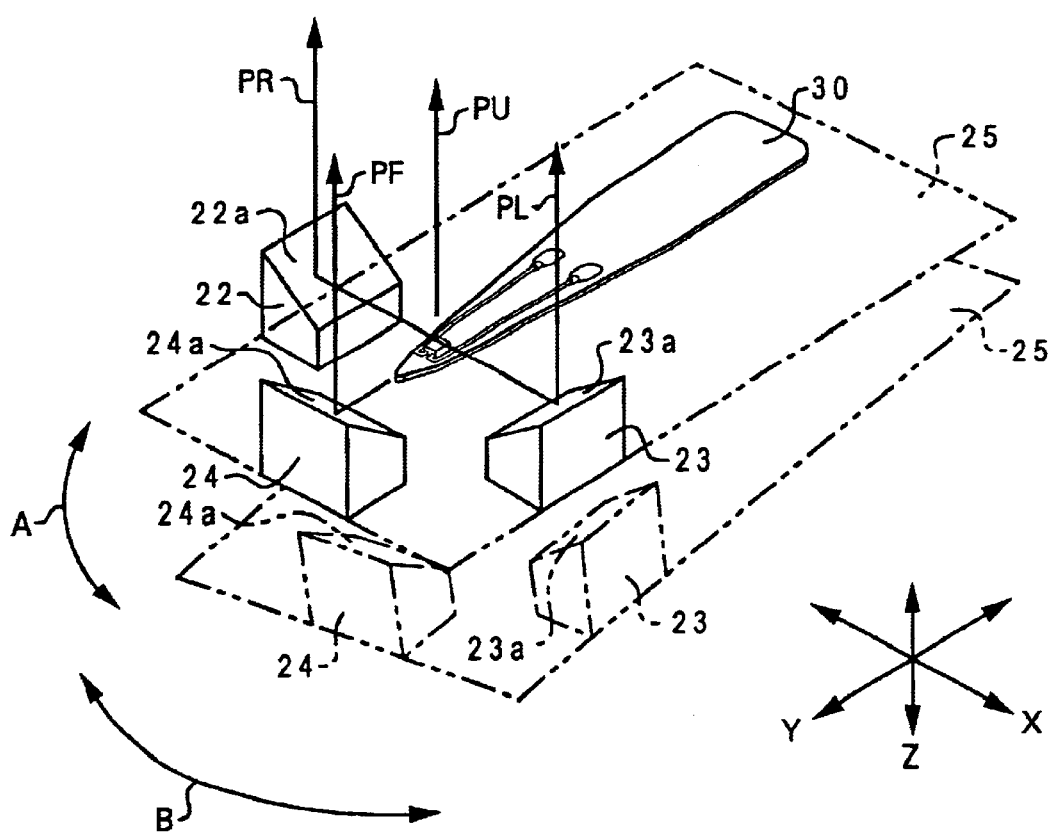
FIG. 9 is a perspective view showing how an inspection-object supporting portion on a universal base is moved.

FIG. 9 is a perspective view showing how the inspection-object supporting portion 20 on the universal base 11 is moved.

As illustrated in FIG. 9, by operating the universal focus-adjusting lever 12, the inspection-object supporting portion 20 on the universal base 11 is rotated on the vertical rotating shaft 11b and moved in the direction of arrow A approximately parallel to the direction of the optical axis of the objective lens 103 of the optical microscope 100. At the same time, the base plate 25 of the inspection-object supporting portion 20 is likewise move up and down in the vertical direction (=pitch direction). Therefore, even when the upper-face image PU of the head assembly 30 is first brought into focus by operating the focus adjusting handle 106, the right side-face image PR, left side-face image PL, and front-face image PF can be easily brought into focus immediately.

In general, the optical microscope 100 has a predetermined depth (focal depth) in the focal distance. For example, if the optical microscope 100 is within the focal depth range on the focal distance, theoretically it does not need to be focused separately. However, the focal depth range is not too large, although it differs depending on magnifications of the microscope. For instance, the focal depth is about 1.2 mm at 7 magnifications and about 0.15 mm at 30 magnifications. Therefore, no matter how close the mirrorlike surfaces 22a to 24a are moved to the head assembly 30, it is difficult to move closer than 1 mm. In addition, in the case where a point to be inspected is near the central portion of the head assembly 30, the mirrorlike surfaces 22a to 24a cannot be moved closer than the outermost periphery of the head assembly 30. Therefore, in general, the right side-face image PR, left side-face image PL, and front-face image PF cannot be inspected with the upper-face image PU brought into focus.

Figure 10:
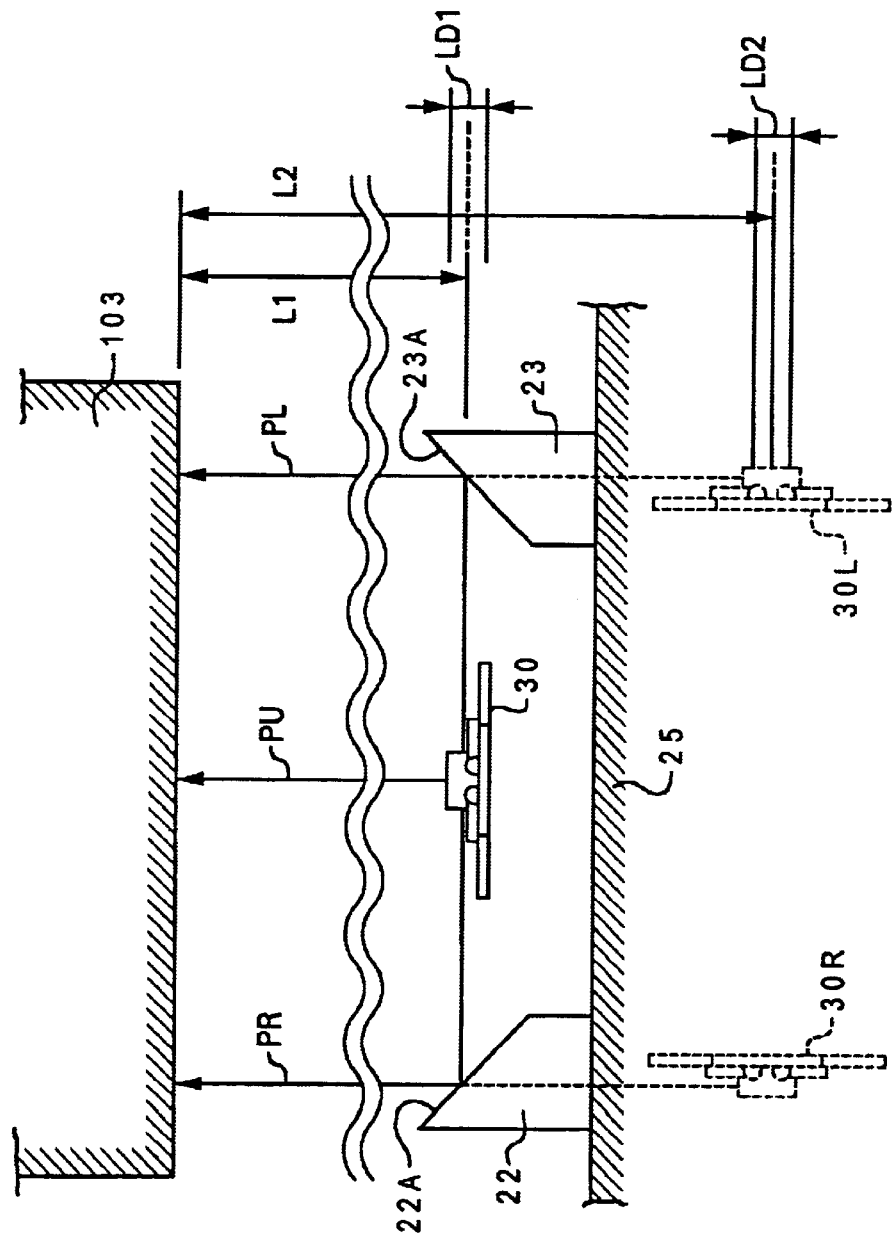
FIG. 10 is a front view showing the relationship between the focal distance and the focal depth in the first embodiment.

FIG. 10 is a front view showing the relationship between the focal distance and the focal depth in the above-mentioned embodiment.

Assume that the focal distance of the upper-face image PU is L1. When the upper-face image PU is focused at the focal distance L1, a range that can be inspected in this condition is in the range of the focal depth LD1. The focal distance L2 of the right side-face image PR and the left side-face image PL, however, is out of the range of the focal depth LD1. Therefore, inspecting the right side-face image PR and the left side-face image PL necessitates the focusing operation again.

Now, a description will be given of the appearance inspecting method that is performed with the appearance inspecting jig 1 of this embodiment, set in the optical microscope 100.

The light emitted from the illuminator 104 is first incident on the upper face of the head assembly 30 which is an inspection object. The light reflected at the upper face of the head assembly 30, as it is, is incident on the objective lens 103. The light emitted from the illuminator 104 is also incident on the front face, right side face, left side face, etc., of the head assembly 30. The light incident on each side face is reflected upward at a right angle and incident on the objective lens 103.

Figure 11:
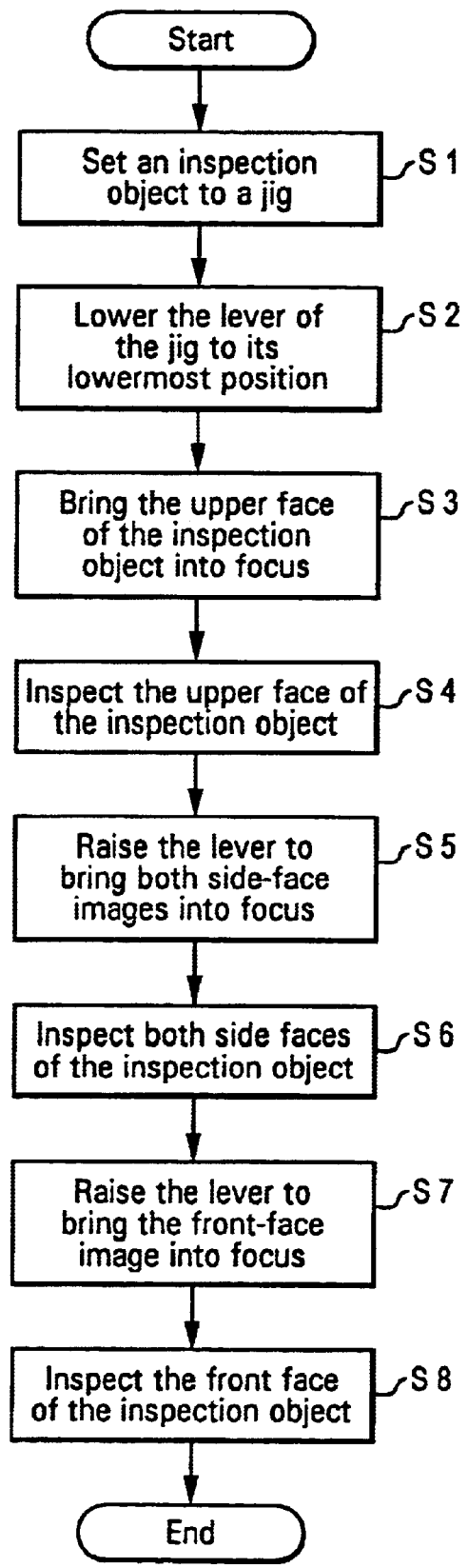
FIG. 11 is a flowchart showing how the inspecting method of the first embodiment is performed.

FIG. 11 is a flowchart showing how the inspecting method employing the appearance inspecting jig 1 of this embodiment is performed.

Note that before making an inspection, the universal base 11 of the appearance inspecting jig 1 of the first embodiment is adjusted and set at the position of the mounting stage of the optical microscope 100.

The inspector first mounts the head assembly 30, on the supporting legs 21 of the inspection-object supporting portion 20 with the inspection surface upward. Then, the inspection-object supporting portion 20 having the head assembly 30 mounted thereon is further mounted on the universal base 11 (step S1). At this stage, the upper-face image PU, right side-face image PR, left side-face image PL, and front-face image PF of the head assembly 30 are within the visual field of the optical microscope 100. However, any image is out of focus.

Next, the inspector lowers the universal focus-adjusting lever 12 to the lowermost position in the up-and-down direction (pitch direction) (step S2). At that position, the inspector brings the upper-face image PU of the head assembly 30 (inspection object) into focus by operating the focus adjusting handle 106 (step S3). In this state, the inspector inspects a defect on the upper face of the head assembly 30 (inspection object) (step S4).

Next, the inspector brings the right and left side-face images PR and PL into focus, while gradually raising the universal focus-adjusting lever 12 in the up direction (step S5). In this state, the inspector inspects defects on the right and left side faces of the head assembly 30 (inspection object)(step S6).

Furthermore, the inspector brings the front-face image PF into focus, while gradually raising the universal focus-adjusting lever 12 in the up direction (step S7). In this state, the inspector inspects a defect on the front face of the head assembly 30 (inspection object)(step S8).

If the inspection of the head assembly 30 being set in the microscope 100 is completed, the inspection-object supporting portion 20 having the head assembly 30 mounted thereon is removed from the microscope 100. Then, the head assembly 30 is removed from the inspection-object supporting portion 20. Subsequently, the next head assembly 30 is mounted on the inspection-object supporting portion 20, and the inspection-object supporting portion 20 is mounted on the universal base 11. In this state, the subsequent inspection is carried out by repeating the above-mentioned steps.

In the event that a plurality of inspection-object supporting portions 20 can be prepared, a plurality of head assemblies 30 may be separately mounted on the inspection-object supporting portions 20, and the subsequent inspections made only by exchanging the inspection-object supporting portion 20.

Now, a description will be made of the visual field of the optical microscope 100 in the case where the inspector operates the optical microscope 100 and appearance inspecting jig 1, as described above.

Figure 12:
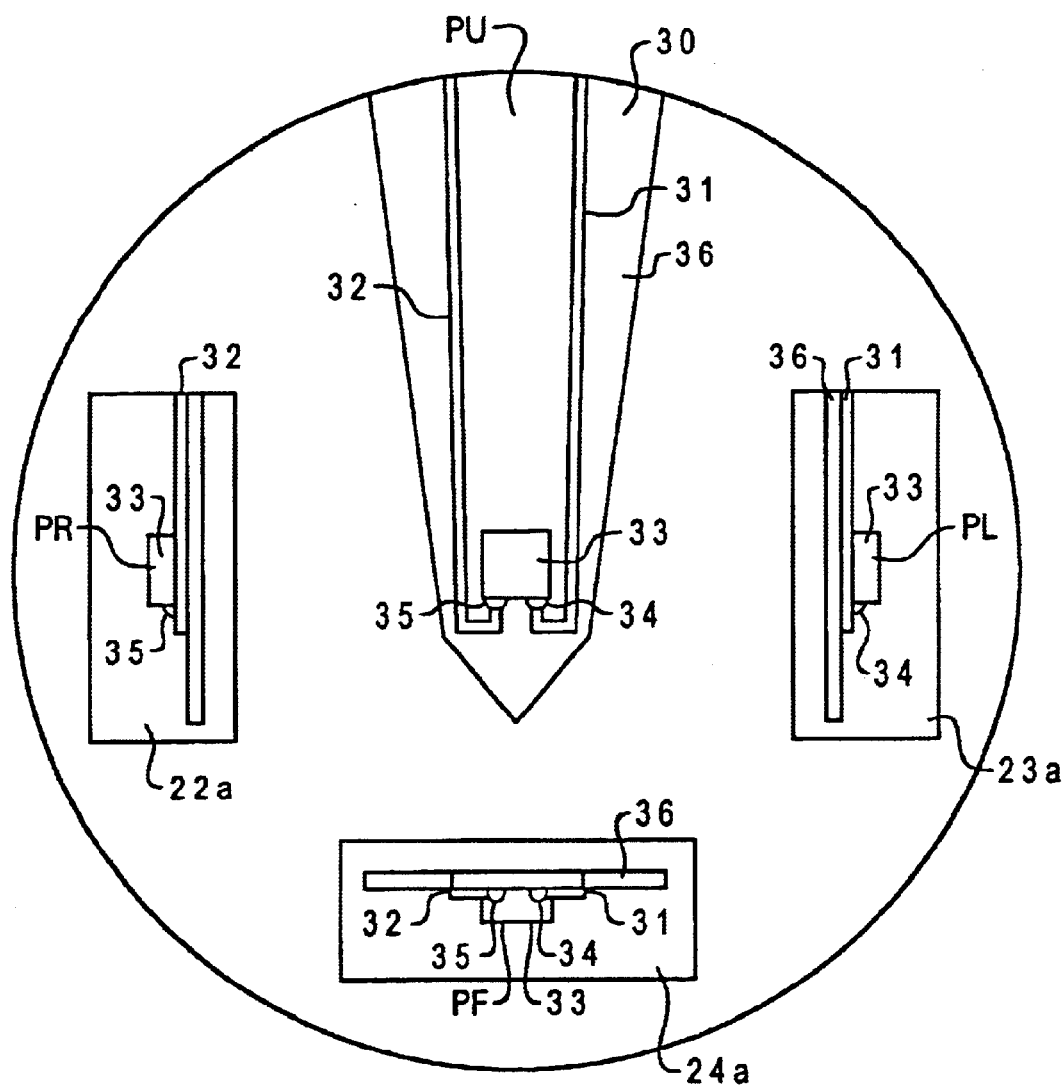
FIG. 12 is a diagram showing the images that are visible to the optical microscope in the first embodiment.

FIG. 12 is a diagram showing a combination of visual-field images that are visible to the ocular lens 101 when the upper-face image PU, right side-face image PR, left side-face image PL, and front-face image PF of the head assembly 30 are separately in focus. That is, in the actual appearance inspection, all the images shown in FIG. 12 are not visible in focus at one time.

At the stage of the above-mentioned steps S3 and S4, only the upper-face image PU in FIG. 12 is in focus, and the other images are out of focus. At this stage, for example, with the upper-face image PU, it is inspected whether the left wiring 31 has securely been connected at the left connecting portion 34 to the head 33, and it is inspected whether the right wiring 32 has securely been connected at the right connecting portion 35 to the head 33.

Next, with the operation of gradually raising the universal focus-adjusting lever 12 upward, at the stage of the steps S5 and S6 only the right and left side-face images PR and PL are brought into focus, and the other images are out of focus. At this stage, for instance, whether the left wiring 31 has securely been connected at the left connecting portion 34 to the head 33 is inspected by the left side-face image PL, and whether the right wiring 32 has securely been connected at the right connecting portion 35 to the head 33 is inspected by the right side-face image PR.

Furthermore, with the operation of gradually raising the universal focus-adjusting lever 12 upward, at the stage of the steps S7 and S8 only the front-face image PF is brought into focus, and the other images are out of focus. At this stage, for instance, whether the left wiring 31 has securely been connected at the left connecting portion 34 to the head 33 is inspected by the front-face image PF, and whether the right wiring 32 has securely been connected at the right connecting portion 35 to the head 33 is inspected by the front-face image PF.

While, in this embodiment, the right and left side-face images and the front-face image of the head assembly 30, in addition to the upper-face image, have been inspected, only the upper-face image PU and one side-face image may be inspected or only the upper-face image PU and front-face image PF inspected, by arbitrarily changing the installation of the mirror blocks 22 to 24.

Thus, according to this embodiment, when carrying out the appearance inspection in many directions, only a series of operations for gradually raising the universal focus-adjusting lever 12 upward are required, after the inspector first brings the upper-face image PU of the head assembly 30 into focus with the focus adjusting handle 106. Therefore, the inspector can readily inspect the right side face, left side face, and front face of the head assembly 30 without changing many times the manner of holding the head assembly 30.

In addition, this embodiment is capable of preventing damage due to the contact between the head assembly 30 and objective lens 103 in the course of inspection, destruction of the head assembly 30 due to static electricity stored in the inspector's body, and a reduction in the quality due to dirt on the head assembly 30, because the inspector does not directly hold the head assembly 30.

Moreover, in this embodiment, since the inspection-object supporting portion 20 is detachably mounted on the universal base 11, the head assembly 30 is fixed to the supporting legs 21 of the inspection-object supporting portion 20 at a place away from the optical microscope 100 and then the inspection-object supporting portion 20 is mounted on the universal base 11. With this operation, mechanical damage, etc., in mounting the head assembly 30 on the appearance inspecting jig 1 can also be prevented.

Now, a description will be given of an appearance inspecting jig of a second embodiment of the present invention.

In the above-mentioned first embodiment, there is no necessity to inspect a surface on which the head 33 is not disposed, because wiring in the head assembly 30 is performed on a surface where the head 33 is disposed. However, there are instances where in some of the head assemblies, wiring is performed on a surface on which the head is not disposed. Hence, in the second embodiment that is to be described later, a description will be made of an appearance inspecting jig which is capable of inspecting the lower face of the head assembly 30 in addition to the upper face, right side face, left side face, and front face of the head assembly 30 of the first embodiment.

Figure 13:
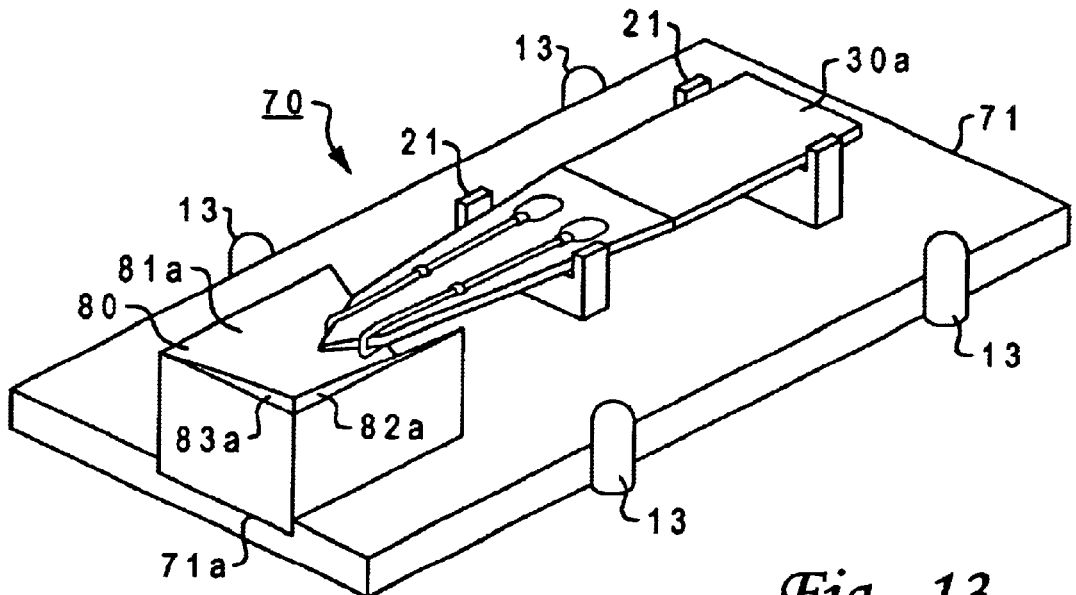
FIG. 13 is a perspective view showing an inspection-object supporting portion of a second embodiment of the present invention.

FIG. 13 is a perspective view showing an inspection-object supporting portion 70 of a second embodiment of the present invention that replaces the inspection-object supporting portion 20 of the first embodiment shown in FIG. 5.

In FIG. 13, the same reference numerals are applied to parts having the same function as the inspection-object supporting portion 20 of the first embodiment of FIG. 5 to avoid redundancy. The mirror block employed in the second embodiment is a three-faced mirror block wherein the three mirror blocks employed in the first embodiment are united in a body. The details will be described later with the drawings. In addition, in the second embodiment, a head assembly 30a is fixed at a position shifted laterally from the center of the three-faced mirror block 80. This is also to be described in detail later with the drawings.

The supporting portion 21 in the second embodiment is capable of supporting, for example, the head assembly 30a so that the lower-face image of the head assembly 30a is reflected at the mirrorlike surface 81a of the three-faced mirror block 80, by moving the head assembly 30a in parallel to the center line of the left and right mirrorlike surfaces 81a and 82a of the three-faced mirror block 80 and to the upper flat surface 11u. The lower-face image of the head assembly 30a reflected at the mirrorlike surface 81a is again reflected at the mirrorlike surface 82a and guided to the objective lens 103. This is to be described later with FIG. 15.

As shown in FIG. 13, a recess 71a corresponding to the dimensions of the bottom surface of the three-faced mirror block 80 is provided on the base plate 25 in order to fix the mirror block 80 at a predetermined position. The three-faced mirror block 80 is fitted into the recess 71a in such a manner that (1) the right mirrorlike surface 81a is disposed so that the right side-face image of the head assembly 30a can be guided to the objective lens 103 of the optical microscope 100; (2) the left mirrorlike surface 82a is disposed so that the left side-face image of the head assembly 30a can be guided to the objective lens 103 of the optical microscope 100; and (3) a front mirrorlike surface 83a is disposed so that the front-face image of the head assembly 30a can be guided to the objective lens 103 of the optical microscope 100.

Now, the configuration of the three-faced mirror block 80 will be described in further detail.

Figure 14:
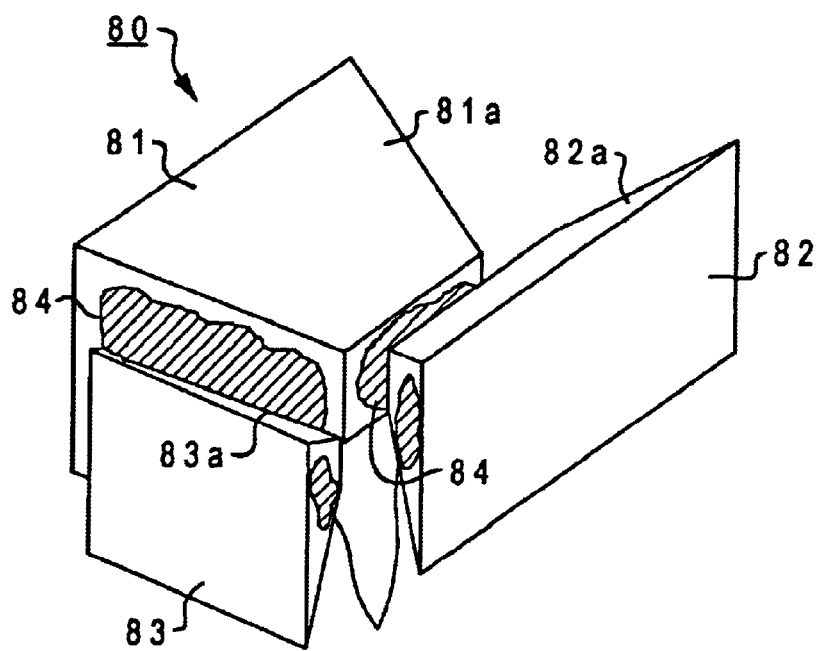
FIG. 14 is a diagram showing the configuration of the three-faced mirror block shown in FIG. 13.

FIG. 14 is a diagram showing the configuration of the three-faced mirror block 80 shown in FIG. 13.

The three-faced mirror block 80 shown in FIG. 14 is composed of a right mirror block 81 for reflecting the image of the right side face of the head assembly 30a, a left mirror block 82 for reflecting the image of the left side face of the head assembly 30a, and a front mirror block 83 for reflecting the image of the front face of the head assembly 30a. The mirror blocks 81 to 83 are designed so that each of the mirrorlike surfaces 81a to 83a is capable of reflecting the image of each side face of the head assembly 30a and that the blocks 81 to 83 are united in a body. In addition, the joining surfaces of the mirror blocks 81 to 83 are bonded by a conductive adhesive 84.

Figure 15:
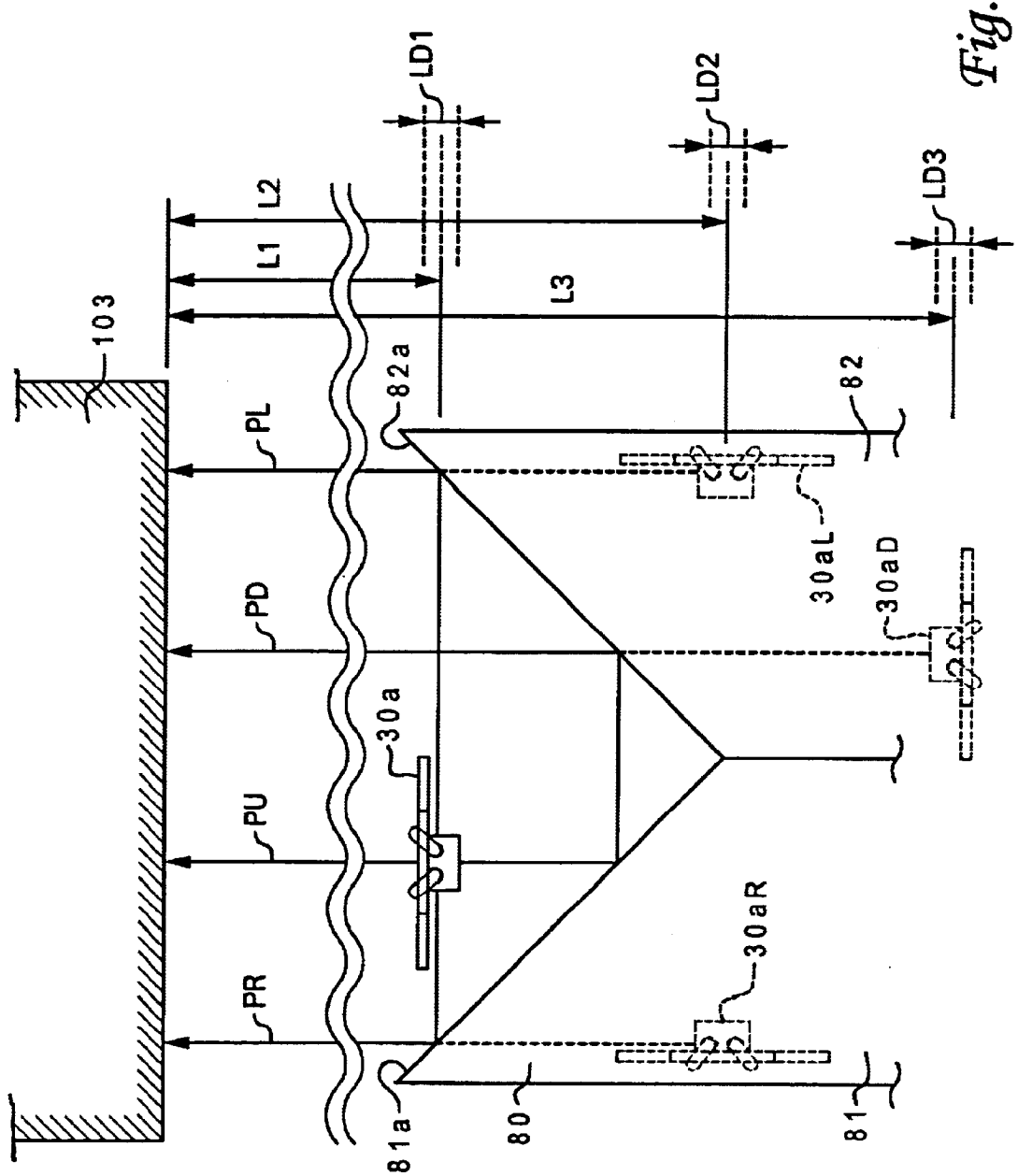
FIG. 15 is a front view showing the relationship between the focal distance and focal depth in the second embodiment.

FIG. 15 is a front view showing the relationship between the focal distance and focal depth in the second embodiment.

Since the upper-face image PU and the left and right side-face images PL, PR are the same as those in the first embodiment shown in FIG. 10, their description is omitted. The lower-face image PD of the head assembly 30a is first reflected at the mirrorlike surface 81a of the right mirror block 81 of the three-faced mirror block 80 and changed 90 degrees in direction. Then, the lower-face image PD is again reflected at the mirrorlike surface 82a of the left mirror block 82 and changed 90 degrees in direction and is incident on the objective lens 103. The focal distance L3 of the lower-face image PD, therefore, becomes longer than the focal distance L2 of the left and right side-face images.

Therefore, in the inspecting method in the second embodiment, a step of raising the universal focus-adjusting lever 12 again to bring the lower-face image PD into focus, and a step of inspecting the lower face of an inspection object by use of the lower-face image PD, are added to the last step of the inspecting method of the first embodiment.

Now, the visual field of the optical microscope 100 in the second embodiment will be described.

Figure 16:
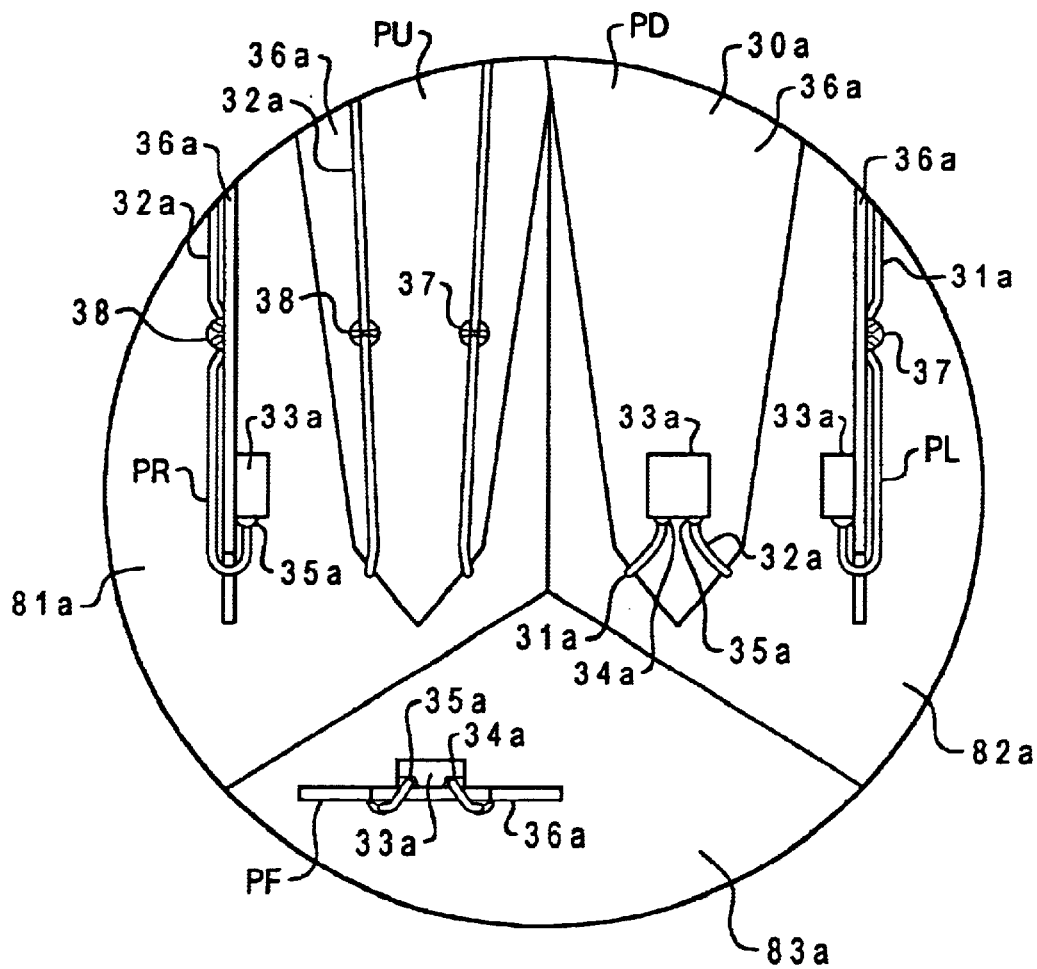
FIG. 16 is a diagram showing the images that are visible to the optical microscope in the second embodiment.

FIG. 16 is a diagram showing a combination of visual-field images that are visible to the ocular lens 101 when the upper-face image PU, right side-face image PR, left side-face image PL, front-face image PF, and the head assembly 30a are separately in focus.

At the time the universal focus-adjusting lever 12 has been lowered to its lowermost position, only the upper-face image PU in FIG. 16 is in focus, and the other images are out of focus. At this stage, for example, with the upper-face image PU, it is inspected whether left wiring 31a has been fixed by a left-wiring fixing portion 37, and it is inspected whether right wiring 32a has been fixed by a right-wiring fixing portion 38.

Next, with the operation of gradually raising the universal focus-adjusting lever 12 upward, only the right and left side-face images PR and PL in FIG. 16 are brought into focus, and the other images are out of focus. At this stage, for instance, whether the left wiring 31a has been fixed by the left-wiring fixing portion 37 is inspected by the left side-face image PL, and whether the left wiring 31 a has securely been connected at a left connecting portion 34a to a head 33a is inspected by the left side-face image PL. Likewise, whether the right wiring 32a has been fixed by the right-wiring fixing portion 38 is inspected by the right side-face image PR, and whether the right wiring 32a has securely been connected at a right connecting portion 35a to the head 33a is inspected by the right side-face image PR.

Furthermore, with the operation of gradually raising the universal focus-adjusting lever 12 upward, only the front-face image PF in FIG. 16 is brought into focus, and the other images are out of focus. At this stage, for instance, whether the left wiring 31a has securely been connected at the left connecting portion 34a to the head 33a is inspected by the front-face image PF, and whether the right wiring 32a has securely been connected at the right connecting portion 35a to the head 33a is inspected by the front-face image PF.

Moreover, with the operation of gradually raising the universal focus-adjusting lever 12 upward, only the lower-face image PD in FIG. 16 is brought into focus, and the other images are out of focus. At this stage, for instance, whether the left wiring 31a has securely been connected at the left connecting portion 34a to the head 33a is inspected by-the lower-face image PD, and whether the right wiring 32a has securely been connected at the right connecting portion 35a to the head 33a is inspected by the lower-face image PD.

In this manner, the second embodiment is capable of readily inspecting the lower face of the head assembly 30a in addition to the right side face, left side face, and front face, by carrying out a series of operations for gradually raising the universal focus-adjusting lever 12 upward, after the inspector first brings the upper-face image PU of the head assembly 30a into focus with the focus adjusting handle 106.

Now, a description will be given of an appearance inspecting jig of a third embodiment of the present invention.

In the above-mentioned first and second embodiments, only the single head assembly 30 or 30a has been fixed to the inspection-object supporting portion 20 or 70. However, for example, if a plurality of head assemblies 30a can be set to a jig, the second head assembly 30a necessitates only the operation of adjusting the universal focus-adjusting lever 12 so that the second head assembly 30a appears within the visual field of the microscope. Therefore, because the operation in step S1 shown in FIG. 11 (which is a time-consuming operation of setting an inspection object to a jig) can be omitted, the inspecting operation can be more efficiently performed. Hence, in the third embodiment to be described later, a description will be made of an appearance inspecting jig which is capable of inspecting a plurality of head assemblies 30a by a single setting operation.

Figure 17:
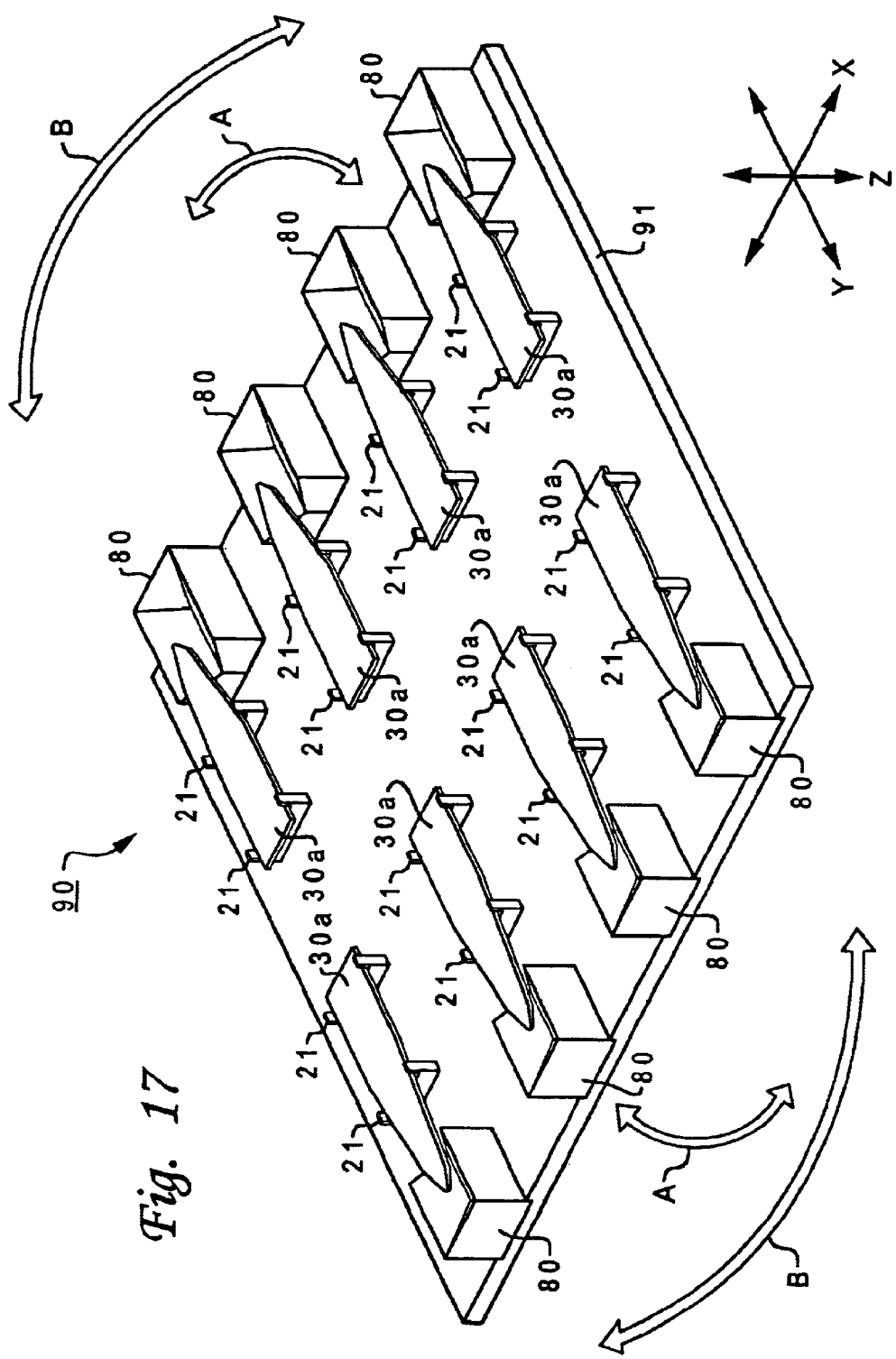
FIG. 17 is a perspective view showing an inspection-object supporting portion of a third embodiment of the present invention.

FIG. 17 is a perspective view showing an inspection-object supporting portion 90 of the third embodiment of the present invention that replaces the inspection-object supporting portion 70 of the second embodiment shown in FIG. 13.

In FIG. 17, the same reference numerals are applied to parts having the same function as the inspection-object supporting portion 70 of the second embodiment of FIG. 13 for avoiding redundancy. A universal base 11 employed in the third embodiment is larger in size than the first and second embodiments so that a plurality of head assemblies 30a can be inspected by a single setting operation.

As illustrated in FIG. 17, the third embodiment is characterized in that a plurality of sets of a three-faced mirror block 80 and supporting legs 21 are mounted on a base plate 91 so that a plurality of head assemblies 30a can be fixed.

The inspecting method in the third embodiment is similar in inspection of the first head assembly 30a to the inspecting method in the second embodiment, as stated above, but differs from the first and second embodiments in that for the inspection of the second head assembly 30a and subsequent head assemblies 30a, the operation in step S1 shown in FIG. 11 is replaced with the step of operating the universal focus-adjusting lever 12 so that the subsequent head assembly 30a is visible within the visual field of the optical microscope. The process of operating the universal focus-adjusting lever 12 so that the subsequent (second) head assembly 30a is visible within the visual field of the optical microscope is easier and takes less time than the process, in step S1 of FIG. 11, of setting an inspection object to the jig. Thus, the inspecting operation can be speeded up.

In this manner, the third embodiment is capable of easily inspecting the upper, right, left, and lower faces of the head assembly 30a and also efficiently performing the operation of inspecting a plurality of head assemblies 30a, because the inspector can set the plurality of head assemblies 30a to the appearance inspecting jig at a time.

While, in the above-mentioned embodiments, the upper flat surface 11u of the universal base 11 has been moved in the up-and-down direction and right-and-left direction (directions of arrows A and B in FIG. 4) by manipulation of the universal focus-adjusting lever 12 provided as an assisting means, the present invention is not limited to this. For example, the assisting means may be dial manipulation through gears, etc. It may also be electrical manipulation (switch) employing a high-precision stepping motor, etc.

In addition, in the aforementioned embodiments the mirrorlike surface of each of the reflecting means has an inclined angle of approximately 45 degrees with respect to the upper flat surface 11u of the base 11. This is because there are cases where the inclined angle depends on the positional relationship of the mirrorlike surface with respect to the actual head assembly and does not equal 45 degrees, although the most ideal angle, at which the reflected light (side-face image which travels in the direction parallel to the upper flat surface 11u) from the side face of the head assembly (which is an inspection object) is incident on the objective lens 103 of the optical microscope 100 in parallel to the light (upper-face image which travels in the direction perpendicular to the upper flat surface 11u) reflected at the upper face of the head assembly, is 45 degrees. The angle of this mirrorlike surface does not always need to be 45 degrees, as long as the right or left side-face image incident in the horizontal direction is reflected upward at a right angle and travels in the same direction as that of the light reflected at the upper face of the head assembly. Depending on the positional relationship of the mirrorlike surface to the head assembly, there are instances where the reflected light of the right or left side-face image travels in the same direction as that of the reflected light of the upper-face image when the mirrorlike surface is disposed at an angle slightly less than 45 degrees to the upper flat surface 11u.

What is claimed is:

1. A jig for inspecting an object with an optical microscope, comprising:

a base, having an upper flat surface in an x-y plane which becomes a mounting stage of said optical microscope;

a member for moving said upper flat surface at least in a direction approximately parallel to a direction of an optical axis of an objective lens of said optical microscope in order to focus said optical microscope on an inspection portion of said object mounted on said upper flat surface, the member comprising a vertical pivot assembly mounted to the base and having a z-axis, a bracket mounted to the vertical pivot assembly opposite the base such that the bracket is rotatable about the z-axis relative to the base in the x-y plane, a horizontal pivot assembly mounted to the bracket and having an x-axis, and a platform for supporting the object and allowing a top view of the object to be visible in a z-direction, the platform being mounted to the horizontal pivot assembly opposite the bracket such that the platform is rotatable about the x-axis relative to the bracket in a y-z plane;

an inspection-object supporting portion, provided with a member for supporting said object, which is mounted on said upper flat surface, wherein said inspection-object supporting portion is provided with at least one reflecting mirror, and said reflecting mirror is disposed on said inspection-object supporting portion in such a manner that an image of said object is reflected and visible within a visual field of said optical microscope.

2. The jig of claim 1, wherein the image of the object is selected from the group consisting of a front view, a side view, and a bottom view.

3. The jig of claim 1, wherein the at least one reflecting mirror comprises a plurality of reflector assemblies, each of which reflects a different elevational view of the object in the z-direction.

4. The jig of claim 3, wherein one of the plurality of reflector assemblies reflects a bottom view of the object.

5. The jig of claim 3, wherein two of the plurality of reflector assemblies are left and right reflector assemblies that reflect left and right views, respectively, of the object, and wherein the left and right reflector assemblies abut each other.

6. The jig of claim 5, wherein the object is located closer to one of the left and right reflector assemblies than the other, such that the other of the left and right reflector assemblies also reflects a bottom elevational view of the object.

7. The jig of claim 1, further comprising an electrical ground coupled to the platform for electrically grounding the object.

8. The jig for inspecting an appearance of an object according to claim 1, wherein said reflecting mirror has a shape chamfering one side of a metal or optical block in the form of a rectangular solid from said block, and a chamfered face has an inclined angle of approximately 45 degrees to the upper flat surface of said base.

9. The jig for inspecting an appearance of an object according to claim 1, wherein said reflecting mirror comprises two or more reflecting mirrors so that at least the images of the left and night side faces of said object can be guided to said optical microscope, and each said reflecting mirror and each side face of said object are disposed to face each other.

10. The jig for inspecting an appearance of an object according to claim 9, wherein said two or more reflecting mirrors are united at their lower portions in a body.

11. The jig for inspecting an appearance of an object according to claim 10, wherein the supporting member of said inspection-object supporting portion is capable of supporting said object at a position, moved in parallel to a center line of the right and left reflecting mirrors of said united reflecting mirror and said upper flat surface.

12. The jig for inspecting an appearance of an object according to claim 1, wherein said base has a positioning member for detachably holding said inspection-object supporting portion at a predetermined position on said upper flat surface.

13. The jig for inspecting an appearance of an object according to claim 1, wherein said inspection-object supporting portion is equipped with a plurality of sets of said supporting member and said reflecting mirror.

14. The jig for inspecting an appearance of an object according to claim 1, wherein, when said upper flat surface is assumed to be contained as part of the X-Y plane, the moving member of said base is capable of moving said upper flat surface along said X-Y plane.

15. The jig for inspecting an appearance of an object according to claim 1, wherein said base has a shape which is easy for an inspector to operate in order to facilitate movement of said upper flat surface, and is equipped with an assisting member which is connected directly, or indirectly through an arbitrary drive-force transmitting member, with said upper flat surface.

16. The jig for inspecting an appearance of an object according to claim 1, wherein said base is connected to ground.

17. A method of inspecting an appearance of an object with an optical microscope employing an appearance inspecting jig which includes: a base, having an upper flat surface which becomes a mounting stage of said optical microscope, and also provided with a member for moving said upper flat surface so that said optical microscope is focused at a position of inspection of said object mounted on said upper flat surface; and an inspection-object supporting portion, provided with a member for supporting said object, which is mounted on said upper flat surface; said inspection-object supporting portion being provided with a reflecting mirror that has a plurality of reflective surfaces and is disposed so that at least one side face of said object and said rejecting mirror face each other, said method, comprising steps of:

mounting the object in the jig such that atop of the object is exposed from above, and a bottom, a front, and two sides of the object are viewable from above in the reflective surfaces;

making an inspection with the top of said object moved to a focal position of said optical microscope;

inspecting said at least one side face of said object projected on said reflecting mirror;

adjusting the microscope to a first position such that it is focused directly on the top of the object for inspecting the top of the object;

adjusting the microscope to a second position such that it is focused on reflected images of both sides of the object for inspecting both sides of the object; and adjusting the microscope to a third position such that it is focused on a reflected image of the bottom of the object for inspecting the bottom of the object.

18. The method of claim 17, further comprising the step of adjusting the microscope to a fourth position such that it is focused on a reflected image of the front of the object for inspecting the front of the object.

19. The method of claim 17, wherein the adjusting steps comprise pivoting the jig about horizontal and vertical axes in rotational motions to adjust the microscope to the first, second, and third positions.

* * * * *